(12) United States Patent
Miyano

(10) Patent No.: US 8,391,588 B2
(45) Date of Patent: Mar. 5, 2013

(54) APPARATUS FOR EXAMINING PATTERN DEFECTS, A METHOD THEREOF, AND A COMPUTER-READABLE RECORDING MEDIUM HAVING RECORDED THEREIN A PROGRAM THEREOF

(75) Inventor: Hiroyoshi Miyano, Tokyo (JP)

(73) Assignee: NEC Corporation, Tokyo (JP)

( * ) Notice: Subject to any disclaimer, the term of this patent is extended or adjusted under 35 U.S.C. 154(b) by 972 days.

(21) Appl. No.: 11/813,324

(22) PCT Filed: Jan. 5, 2006

(86) PCT No.: PCT/JP2006/300034
§ 371 (c)(1),
(2), (4) Date: Sep. 22, 2009

(87) PCT Pub. No.: WO2006/073155
PCT Pub. Date: Jul. 13, 2006

(65) Prior Publication Data
US 2010/0002930 A1    Jan. 7, 2010

(30) Foreign Application Priority Data
Jan. 5, 2005  (JP) ................................. 2005-000645

(51) Int. Cl.
*G06K 9/00*    (2006.01)
(52) U.S. Cl. ....................... 382/144; 382/149; 356/237.1
(58) Field of Classification Search .................. 382/144, 382/149, 150, 195; 702/70, 81; 356/237.1–237.5
See application file for complete search history.

(56) References Cited

FOREIGN PATENT DOCUMENTS

| JP | 402010819 A | * | 1/1990 |
|---|---|---|---|
| JP | 05-107728 | | 4/1993 |
| JP | 10-325806 | | 12/1998 |
| JP | 11-211671 | | 8/1999 |
| JP | 2000-348177 | | 12/2000 |
| JP | 2001-283196 | | 10/2001 |
| JP | 2002-202268 | | 7/2002 |
| JP | 2003-090717 | | 3/2003 |
| JP | 2003-121984 | | 4/2003 |
| JP | 2004-037136 | | 2/2004 |
| JP | 2002-107309 | | 4/2004 |
| JP | 2004-177446 | | 6/2004 |
| JP | 2006-014292 | | 1/2006 |
| JP | 2001-272217 | | 7/2007 |
| JP | 2010-256716 A | * | 11/2010 |

* cited by examiner

*Primary Examiner* — Hoa Pham
(74) *Attorney, Agent, or Firm* — Whitham Curtis Christofferson & Cook, PC

(57) ABSTRACT

Utilizing only image information of an observation image and a reference image, a strain amount calculation unit calculates strain parameters. The reference image may be generated from design data or a different observation image. Calculated strain parameters are determined using strain formulation coefficients. A compensated image forming unit strains the reference image or the observation image by the strain amount based on the calculated strain parameters. The compensated image formed in the compensated image forming unit is supplied to an identification unit, which compares the compensated image with the reference image or the observation image, and determines positions where the difference is large to defects.

57 Claims, 26 Drawing Sheets

FIG.4
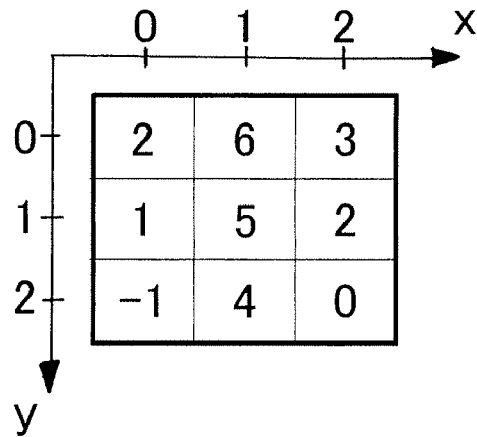
$\delta_x(x,y)$
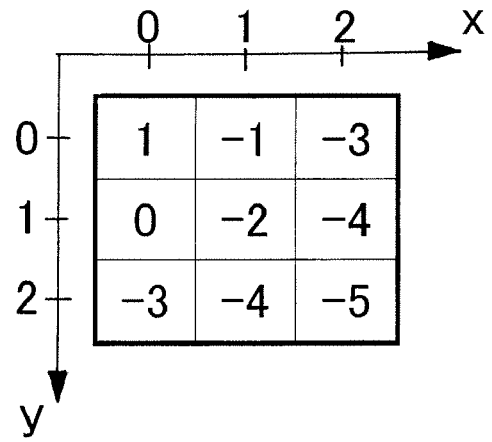
$\delta_y(x,y)$
FIG.5
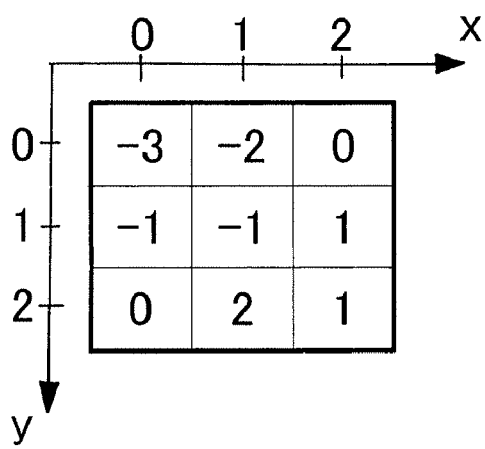
$\delta_x(x,y)$
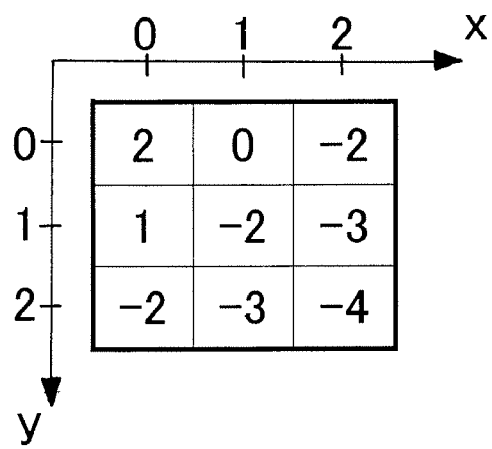
$\delta_y(x,y)$ $|G(x-\delta_x, y-\delta_x) - R(x,y)|$
($\xi = -1$)

$|G(x-\delta_x, y-\delta_x) - R(x,y)|$
($\xi = 0.5$)

$|G(x-\delta_x, y-\delta_x) - R(x,y)|$
($\xi = +0.5$)

$|G(x-\delta_x, y-\delta_x) - R(x,y)|$
($\xi = +1$)

APPARATUS FOR EXAMINING PATTERN DEFECTS, A METHOD THEREOF, AND A COMPUTER-READABLE RECORDING MEDIUM HAVING RECORDED THEREIN A PROGRAM THEREOF

TECHNICAL FIELD

The present invention relates to an apparatus for examining pattern defects, a method thereof, and a computer-readable recording medium having recorded therein a program thereof, and more particularly, to an apparatus for examining pattern defects, a method thereof, and a computer-readable recording medium having recorded therein a program thereof, which are less subject to the strain at the time of picking up an image.

BACKGROUND ART

In the field of examining the pattern of a mask used for a semiconductor integrated circuit such as a reticle or a photomask, higher accuracy is being demanded along with the necessity of miniaturization of the pattern in recent years.

In general, the pattern examination is carried out by forming an observation image which is obtained by irradiating a laser beam or a charged particle beam to a mask, and a reference image which is obtained by performing calculation from design data of corresponding parts, and then comparing thus formed observation image and reference image to find out mismatched parts.

In order to realize the defect examination of high accuracy, the pattern on an observation image is required to accord with the corresponding pattern on a reference image correctly at parts where there is no defect.

Actually, in obtaining an observation image, there is raised a quantity of strain due to the speed unevenness in shifting a stage or problems in the optical system.

Problems in the optical system are as follows. In an optical system that obtains an image by oscillating a beam using an acoustooptic device (AOD) etc. and measuring the beam amount of the transmitted beam, there is raised a strain due to the influence of the AOD, and the degree of strain changes due to the influence of the thermal storage with time. Furthermore, there may be raised a strain in an obtained image due to the strain of a lens which is raised in the peripheral part and central part thereof, and the degree of strain changes due to the influence of the thermal storage with time. Moreover, in case the automatic focus is utilized so as to counter a quantity of warpage raised in a reticle, the focal length is made to fluctuate, and the degree of strain changes according to the fluctuation.

Under the circumstances in which the miniaturization of the pattern is being advanced in recent years, above-described strain, which has not been a problem and not been taken into consideration, cannot be ignored, and the necessity of compensating a strain comes to be indispensable.

As a system to compensate a strain which is raised at the time of obtaining an observation image, in Patent Document 1 and Patent Document 2, there is disclosed a system that measures the shift amount of a stage using a sensor, and compensates a reference image by utilizing the value of the shift amount.

Patent Document 1: JP 2003-121984-A
Patent Document 2: JP 2003-090717-A
Patent Document 3: JP 10-325806-A
Patent Document 4: JP 11-211671-A
Patent Document 5: JP 2000-348177-A Non-Patent Document 1: Pattern classification (second edition), on pages 111 to 113, written by Richard O. Duda and others, translated by Morio Onoe, published by New Technology communications in 2003

Non-Patent Document 2: Pattern classification (second edition), on pages 120 to 125, written by Richard O. Duda and others, translated by Morio Onoue, published by New Technology communications in 2003

DISCLOSURE OF THE INVENTION

Problems to be Solved by the Invention

Problems in the conventional technology are as follows. Since the system measures the shift amount of a stage by using a sensor and carries out the compensation for a strain, a special sensor is required to measure the shift amount of a stage, and only a strain which is raised when a stage is shifted can be compensated. Thus, the system cannot be employed in an arbitrary image-obtaining system, and a strain resulting from the optical system other than the stage shifting cannot be compensated.

In the invention disclosed in Patent Document 5, since a compensation table is formed using a mask which is different from a mask to be examined, this invention is weak in variation per hour when the mask is changed.

It is therefore an object of the present invention to realize examining defects with high accuracy by compensating a strain of an obtained image utilizing only image information of an obtained image and a reference image.

Means for Solving the Problems

The above object can be attained by providing an apparatus for examining pattern defects that expresses the state of a strain from a paired observation image and reference image using a small number of parameters, and estimates the parameters of small number from a paired observation image and reference image at the time of examination to calculate a strain, and then compensates the strain.

According to the present invention, there is provided an apparatus for examining pattern defects including: a strain amount calculation unit that compares a reference image which is obtained from design information and an observation image so as to estimate a strain amount; a strained image forming unit that forms a strained image which is obtained by straining the reference image using the strain amount; and an identification unit that compares the strained image and the observation image so as to identify the defect of a pattern.

According to the present invention, there is also provided an apparatus for examining pattern defects including: a strain amount calculation unit that compares an observation image and a reference image which is obtained from design information so as to estimate a strain amount; a strained image forming unit that forms a compensated image which is obtained by compensating the observation image using the strain amount; and an identification unit that compares the compensated image and the reference image obtained from design information so as to identify the defect of a pattern.

According to the present invention, there is also provided an apparatus for examining pattern defects including: a strain amount calculation unit that compares an observation image and another observation image that is defined as a reference image so as to estimate a strain amount; a strained image forming unit that forms a compensated image which is obtained by compensating the observation image using the strain amount; and an identification unit that compares the compensated image and the reference image so as to identify the defect of a pattern.

According to the present invention, there is also provided an apparatus for examining pattern defects including: a strain amount calculation unit that compares an observation image and a reference image which is obtained from design information, or an observation image which is different from the observation image so as to estimate a strain amount; a compensated image forming unit that forms a compensated image which is obtained by compensating one of the images which is used for the comparison using the strain amount; and an identification unit that compares the compensated image and the other of the images which is used for the comparison so as to identify the defect of a pattern.

According to the apparatus for examining pattern defects, estimating the strain amount may be performed every time each image is examined.

According to the apparatus for examining pattern defects, estimating the strain amount may be performed every predetermined time period.

According to the apparatus for examining pattern defects, the observation image may be an image which is obtained by scanning a processed pattern using a laser beam or a charged particle beam.

According to the apparatus for examining pattern defects, the reference image may be obtained by taking the influence of an optical system at the time of obtaining the observation image into consideration with respect to pattern information included in the design information.

According to the apparatus for examining pattern defects, the strain may be expressed by a small dimension.

According to the apparatus for examining pattern defects, the strain amount calculation unit may utilize the interpolation processing in estimating the strain amount.

According to the apparatus for examining pattern defects, in the interpolation processing, at least the linear interpolation or bicubic interpolation may be utilized.

According to the apparatus for examining pattern defects, the strain amount calculation unit may utilize the approximate calculation by the Taylor expansion in estimating the strain amount.

According to the apparatus for examining pattern defects, the strain may be expressed by a plurality of Gaussian distributions.

According to the apparatus for examining pattern defects, the strain may be expressed by a plurality of sinusoidal waves.

According to the apparatus for examining pattern defects, the strain may be expressed by a plurality of monomials or multinomials.

According to the apparatus for examining pattern defects, the strain may be expressed by obtaining the average value from multiple strained data which has been obtained in advance, and utilizing the average value.

According to the apparatus for examining pattern defects, the strain may be expressed by obtaining the covariance matrix from multiple strained data which has been obtained in advance, and utilizing the result of performing the principal component analysis for the covariance matrix.

According to the apparatus for examining pattern defects, in estimating the covariance matrix, the EM algorithm may be employed.

According to the apparatus for examining pattern defects, the strain amount calculation unit may employ the method of minimizing the sum of squares of the pixel value difference between the two compared images in estimating the strain amount.

According to the apparatus for examining pattern defects, the strain amount calculation unit may employ the method of minimizing the total of the sum of squares of the pixel value difference between the two compared images, and the sum of function values with the value of the strain amount set to an argument in estimating the strain amount.

According to the apparatus for examining pattern defects, the strain amount and a strain amount which has been stored in advance may be compared, and it may be determined that the strain amount is abnormal in case the difference is sufficiently large.

According to the apparatus for examining pattern defects, the strain amount calculation unit may variably set up the dimension for the estimation according to the contents of the compared images in estimating the strain amount.

Advantages of the Invention

The first advantageous effect of the present invention is that the present invention does not depend on the system of obtaining images.

The reason is that a strain amount is obtained from only a paired obtained image and reference image.

The second advantageous effect is that examining defects with high accuracy can be realized.

The reason is that a strain arising from not only the stage shifting but also arbitrary attributes can be compensated.

BRIEF DESCRIPTION OF THE DRAWINGS

FIG. 4 shows a view of an example of strain amounts;

FIG. 5 shows a view of an example of strain amounts;

DESCRIPTION OF THE SYMBOLS

Figure 1:
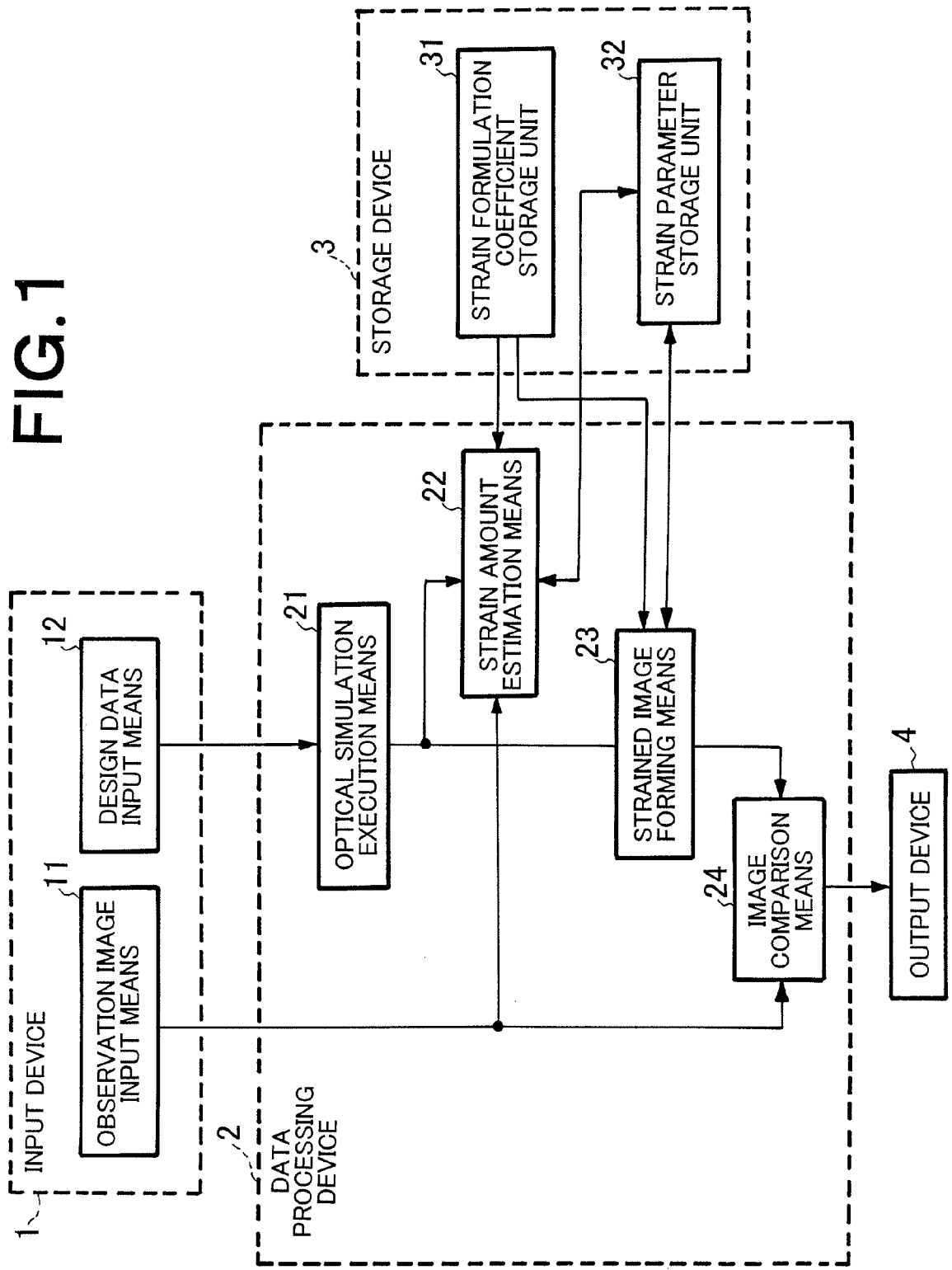
FIG. 1 shows a block diagram indicative of the configuration of the best mode of the first embodiment according to the present invention.

1 Input device
2 Data processing device
3 Storage device
4 Output device
5 Data processing device
8 Defect examination program
11 Observation image input means
12 Design data image input means
13 Comparison observation image input means
21 Optical simulation execution means
22 Strain amount estimation means
23 Strained image forming means
24 Image comparison means
25 Strained image compensation means

BEST MODE FOR CARRYING OUT THE INVENTION

Hereinafter, the best mode to implement the present invention will be described in detail referring to the accompanying drawings.

The present invention will further be described below concerning the best mode with reference to the accompanying drawings.

Referring to FIG. 1, the first best mode of the present invention includes an input device 1 that inputs an image, a data processing device 2 that operates under the control of programs, a storage device 3 that stores information, and an output device 4 such as a display or a printer.

The input device 1 includes an observation image input means 11 and a design data input means 12.

The observation image input means 11 picks up an image of a mask to be examined to find out defects thereof as an observation image by scanning the mask using a laser beam or a charged particle beam, and converting an amount of light to an electric signal using a CCD, etc. In this embodiment, an image that is taken in by the observation image input means 11 is defined as R (x, y). The means to obtain an observation image in the observation image input means 11 is not restricted to a transmission optical system, and there is no problem in case a reflection optical system is employed.

The design data input means 12 takes in design data of a mask to be examined to find out defects thereof.

The storage device 3 includes a strain formulation coefficient storage unit 31 and a strain parameter storage unit 32.

The strain formulation coefficient storage unit 31 has stored therein coefficients which are necessary in calculating a strain. Hereinafter, amounts which are stored in the strain formulation coefficient storage unit 31 are referred to as strain formulation coefficients. Specifically, the strain formulation coefficients are composed of coefficients which are necessary in formulating a strain in the "x" direction and coefficients which are necessary in formulating a strain in the "y" direction for the respective positions (x, y) of an image. Hereinafter, both the number of strain formulation coefficients which are necessary in formulating a strain in the "x" direction and the number of strain formulation coefficients which are necessary in formulating a strain in the "y" direction for the respective positions (x, y) of an image are set to "K". Furthermore, "K" pieces of strain formulation coefficients which are necessary in formulating a strain in the "x" direction are defined as wk (x, y) (where k=1, . . . , K). Moreover, K" pieces of strain formulation coefficients which are necessary in formulating a strain in the "y" direction are defined as vk (x, y) (where k=1, . . . , K).

It is assumed in this embodiment that both the number of strain formulation coefficients which are necessary in formulating a strain in the "x" direction and the number of strain formulation coefficients which are necessary in formulating a strain in the "y" direction are set to "K". On the other hand, the numbers may be different from each other. In case the numbers are different from each other, "0"s are added as strain formulation coefficients for the smaller number to set the number to "K" pieces, and the same manner, which is employed under the assumption that the numbers are equal to each other, may be employed.

The strain parameter storage unit 32 has stored therein "K−1" pieces of parameters which express the state of strain at the time of examining a mask. Hereinafter, the "K−1" pieces of parameters stored in the strain parameter storage unit 32 are referred to as strain parameters, and are defined as ξk (where k=1, . . . , K−1).

The strain of an observation image that is obtained by an optical system at the time of examining a mask can be obtained using two kinds of "K" pieces of strain formulation coefficients from the "K−1" pieces of strain parameters.

Specifically, the strain amounts at a point (x, y) of an observation image are set to δx (x, y), δy (x, y).

The strain amounts δx (x, y), δy (x, y) are obtained by the linear sum as follows.

[Mathematical expression 1]
$$\delta_x(x, y) = \sum_{k=1}^{K-1} \xi_k w_k(x, y) + w_k(x, y)$$

$$\delta_y(x, y) = \sum_{k=1}^{K-1} \xi_k v_k(x, y) + v_k(x, y)$$

The strain amount estimation itself is operable even if the strain formulation coefficients wk (x, y) and vk (x, y) (where k=1, . . . , K) are functions of any form. The better manner of setting up the strain formulation coefficients will be explained hereinafter.

As a first example, assuming that "K" is an odd number which is 3 or more, and (K−1)/2 pieces of points (xk, yk) (where k=1, . . . , (K−1)/2) and one value σ are given in advance, using an isotropic Gaussian distribution in which σ2 is the variance with the (K−1)/2 pieces of points (xk, yk) (where k=1, . . . , (K−1)/2) being the center, as follows, it can be considered that in case of k=1, . . . , (K−1)/2, it is set up that wk=Gauss2k (x, y) and vk=0, and in case of k=(K−1)/2+1, . . . , K−1, it is set up that wk=0 and vk=Gauss2k (x, y), and in case of k=K, it is set up that wk=0 and vk=0.

$$GAUSS2_k(x, y) = \frac{1}{2\pi\sigma^2}\exp\left(-\frac{(x-x_k)^2 + (y-y_k)^2}{2\sigma^2}\right)$$
$$\left(\text{where } k = 1, \ldots, \frac{K-1}{2}\right)$$

[Mathematical expression 2]

It is more desirable that the positions where it is expected that a strain is largely raised are investigated in advance, and the K/2 pieces of points are set to the positions where a strain is largely raised.

Figure 3:
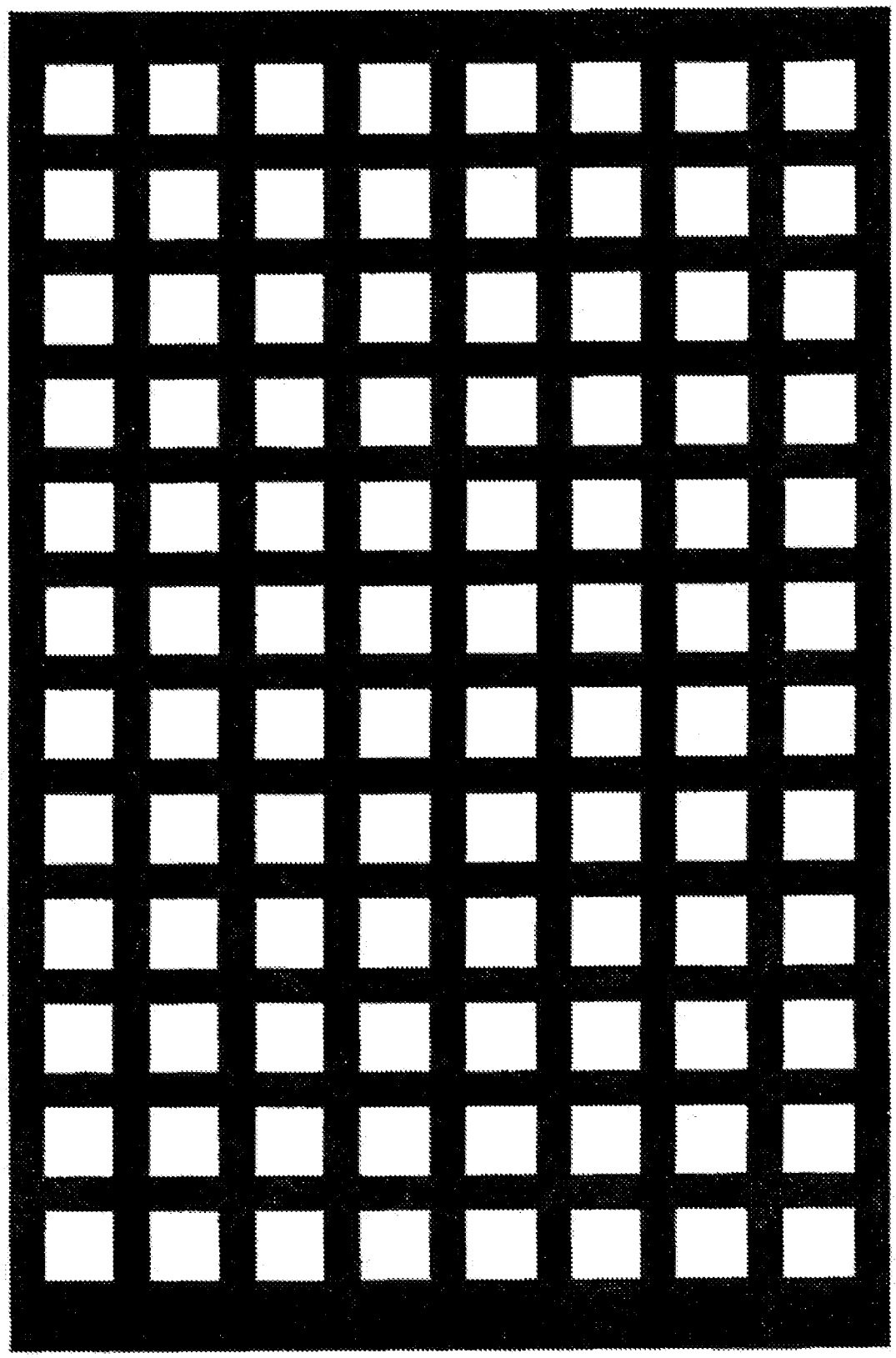
FIG. 3 shows a schematic view of an example of a mask which can easily determine a strain.

As a method for the investigation, for example, there is employed a method of preparing a mask shown in FIG. 3 in which rectangles are lined up at even intervals so as to obtain an observation image of the mask, and comparing the image to judge whether or not the positions of the rectangles in the mask are misaligned by a person, and determining that the positions where the positions of the largely misaligned rectangles are determined to have a large strain is the positions where a strain is largely raised.

It is desirable that the value of σ is set approximately to the distance between the respective points of the selected points or more.

In this case, instead of an isotropic Gaussian distribution, other arbitrary functions such as a multinomial may be used.

Depending on the manner of obtaining an image, there is a possibility that a strain is prone to be raised in only one direction of the "x" direction and "y" direction.

In case of the state in which a strain is prone to be raised in only the "y" direction, assuming that (K−1) pieces of y-coordinate values "yk" (where k=1, . . . , K−1) and one value C are given in advance, using a Gaussian distribution in which σ2 is the variance with the (K−1) pieces of y-coordinate values "yk" (where k=1, . . . , K−1) being the center, as follows, it can be considered that in case of k=1, . . . , K−1, it is set up that wk=0 and vk=Gauss1Yk (x, y), and in case of k=K, it is set up that wk=0 and vk=0.

$$GAUSS1Y_k(x, y) = \frac{1}{\sqrt{2\pi}\,\sigma}\exp\left(-\frac{(y-y_k)^2}{2\sigma^2}\right)$$
$$(\text{where } k = 1, \ldots, K-1)$$

[Mathematical expression 3]

In this case, instead of a Gaussian distribution, other arbitrary functions may be used.

It can be considered that a strain in the "y" direction is raised depending on x-coordinate values. Considering that an image is obtained with a stage being shifted in the "x" direction, there is a possibility that a vibration in the "y" direction of the stage is raised when the stage is shifted in the "x" direction. At this time, depending on x-coordinate values, a strain in the "y" direction is raised.

For example, in case it is considered that the manner of vibration in the "y" direction, which is raised when a stage is shifted in the "x" direction, can be expressed by "K" ways of sinusoidal waves sin (akx+bk) using "K−1" pieces of parameters "ak" (where k=1, . . . , K) and "K−1" pieces of parameters "bk", in case of k=1, . . . , K−1, it is set up that wk=0 and vk=sin (akx+bk), and in case of k=K, it is set up that wk=0 and vk=0.

As another example, it can be considered that the strain formulation coefficients are simply set up by low-dimensional monomials. For example, in case of K=7, monomials 1, "x", and "y" are set up as the strain formulation coefficients as follows.

w1=1, v1=0
w2=x, v2=0
w3=y, v3=0
w4=0, v4=1
w5=0, v5=x
w6=0, v6=y
w7=0, v7=0

When the "K" increased, high-dimensional monomials are employed. For example, in case of K=13, monomials 1, "x", "y", "x2", "xy", and "y2" are set up as the strain formulation coefficients as follows.

w1=1, v1=0
w2=x, v2=0
w3=y, v3=0
w4=x2, v4=0
w5=xy, v5=0
w6=y2, v6=0
w7=0, v7=1
w8=0, v8=x
w9=0, v9=y
w10=0, v10=x2
w11=0, v11=xy
w12=0, v121=y2
w13=0, v13=0

In this case, high-dimensional monomials are also utilized in addition to the monomials used in case of K=7.

In above-described explanation, monomials are set up as the strain formulation coefficients. On the other hand, it is possible to use multinomials of various dimensions instead of the monomials.

Furthermore, as another approach, there may also be considered a method of estimating multiple strain amounts using multiple masks by utilizing some of above-described strain formulation coefficients in advance, and then obtaining better strain formulation coefficients using the result.

Hereinafter, it is determined that the size of a mask to be examined is M×N. Since the strain amounts δx (x, y), δy (x, y) are composed of 2MN pieces of parameters in all, the strain amounts can be expressed by a single vector "δ" of 2MN dimensions.

FIG. 4 shows an example of the strain amounts δx (x, y), δy (x, y) in case of M=3, N=3. In this case, the corresponding vector "δ" can be expressed by a vector of 18 dimensions as follows.

$$\delta=(2,6,3,1,5,2,-1,4,0,1,-1,-3,0,$$
$$-2,-4,-3,-4,-5)^t$$

[Mathematical expression 4]

In this mathematical expression, "t" represents the inversion. Hereinafter, above-described operation of converting two images of M×N to a vector of 2MN dimensions is defined as an operation "T".

Conversely, the strain amounts δx (x, y), δy (x, y) can be restored from the vector "δ". For example, in case the "δ" is expressed as follows, corresponding two images of M×N are expressed as shown in FIG. 5.

$$\delta=(-3,-2,0,-1,-1,1,0,2,1,2,0,-2,1, -2,-3,-2,-3,-4)^t \quad \text{[Mathematical expression 5]}$$

Hereinafter, the operation of forming a pair of images of M×N from a vector of 2MN dimensions is defined as an operation "T−1".

Next, an example of the method of estimating multiple strain amounts using multiple masks by employing the defined operation "T" and operation "T−1", and then obtaining better strain formulation coefficients using the result will be explained.

Firstly, there is considered a method of estimating "D" ways of strain amounts δx (x, y), δy (x, y) using "D" pieces of masks, and obtaining better strain formulation coefficients using the result.

It is determined that "D" ways of strain amounts δx (x, y), δy (x, y) which are calculated using "D" pieces of masks are expressed as δd (d=1, . . . , D) using vectors by the operation "T". The "δd" represents a vector of a strain amount that is calculated using the d-th mask.

Next, the average vector "μ" of "D" pieces of vectors δd (d=1, . . . , D) of 2MN dimensions will be obtained. The "μ" is a vector of 2MN dimensions, and there may be considered a method of setting two images obtained by performing the operation "T−1" to uK (x, y), vK (x, y), respectively.

Alternatively, as is disclosed in the Non-Patent Document 1, the main component analysis is carried out for "D" pieces of vectors δd (d=1, . . . , D) of 2MN dimensions.

The main component analysis can be realized by obtaining the average and covariance matrix from "D" pieces of vectors, and performing the singular value decomposition for thus obtained covariance matrix.

Thus obtained main components are set to vd (d=1, . . . , D). The vd (d=1, . . . , D) are vectors of 2MN dimensions.

There may be considered a method of selecting the "K−1"-th main component from the average vector and the first main component, and setting two images which are obtained by performing the operation "T−1" for the k-th main component to uk (x, y), vk (x, y), and setting two images which are obtained by performing the operation "T−1" for the average "μ" to uK (x, y), vK (x, y). Employing the main component analysis, "K" can be set to a small value, which can bring about a merit that the estimation becomes stable.

The size of strain cannot be estimated in a region where the gradation value is even. The reason is that even if there is a strain or no strain in an even region, the region comes to be even. Accordingly, as above-described "D" pieces of masks, it is desirable to select masks in which there are few even regions.

Alternatively, in case "D" pieces of masks contain masks in which there are many even regions, considering component values of the 2MN vector "δ" corresponding to the values of the δx (x, y), δy (x, y) at a point (x, y) in an even region to be lost data, there may be employed a method of obtaining the average and covariance matrix by utilizing a method of obtaining the average and covariance matrix in case there is loss data using the EM algorithm, which is disclosed in the Non-Patent Document 2, and setting the result to the main component analysis. Employing the EM algorithm, it becomes unnecessary to prepare special "D" pieces of masks, which can bring about a merit that the learning has to be performed by simply selecting "D" pieces of masks which have been examined immediately before.

The data processing device 2 is a device that examines defects, and includes an optical simulation execution means 21, a strain amount calculation means 22, an strained image forming means 23, and an image comparison means 24.

The optical simulation execution means 21 is a means that executes the optical simulation for design data of a mask which is obtained in the design data input means 12 so as to form a reference image. Hereinafter, a reference image that is obtained by the optical simulation execution means 21 is defined as G (x, y).

Since the observation image R (x, y) has a strain, in case the strain in the "x" direction of the observation image is set to "δx", and the strain in the "y" direction thereof is set to "δy", the reference image corresponding to the R (x, y) has to be G (x−δx, y−δy).

The strain amount calculation means 22 estimates the strain parameters that express the amount of a strain raised at the time of obtaining an observation image, using the observation image R (x, y) obtained in the observation image input means 11, the reference image G (x, y) obtained in the optical simulation execution means, and coefficients stored in the strain compensation coefficient storage unit 31.

The strain parameters can be estimated to be obtained by minimizing the following mathematical expression with respect to ξk (k=1, . . . , K−1).

$$S = \sum_x \sum_y (G(x-\delta_x, y-\delta_y) - R(x, y))^2 \quad \text{[Mathematical expression 6]}$$

Alternatively, adding a function f (ξ1, . . . , ξK−1) with respect to the ξk (k=1, . . . , K−1), the strain parameters can be obtained by minimizing the following mathematical expression with respect to ξk (k=1, . . . , K−1).

$$S = \sum_x \sum_y (G(x-\delta_x, y-\delta_y) - R(x, y))^2 + \quad \text{[Mathematical expression 7]}$$
$$f(\xi_1, \ldots, \xi_{K-1})$$

As an example of the f (ξ1, . . . , ξK−1), for example, using a constant "λ" which has been set up in advance, the following mathematical expression can be employed.

$$f(\xi_1, \ldots, \xi_{K-1}) = \lambda \sum_{k=1}^{K-1} \xi_k^2 \quad \text{[Mathematical expression 8]}$$

This is a term to be added so as to prevent the judgment that the strain is too large.

For example, in case it is not appreciated whether or not the strain is large or small when there are many even regions, there is raised an influence of judging that the strain is small. Since the reference image is strained when the strain becomes larger, above-described response is desirable from a viewpoint of the processing amount.

The G (x−δx, y−δy) in above-described Mathematical expression 6 can be obtained by the linear interpolation.

That is, when the maximum integer not exceeding x−δx is set to "X", and the maximum integer not exceeding y−δy is set to "Y", and two parameters "εx", "εy" are defined as εx=x−δx−X, εy=y−δy−Y, the G (x−δx, y−δy) can be obtained as follows.

$$G(x - \delta_x, y - \delta_y) = G(X, Y)(1 - \varepsilon_x)(1 - \varepsilon_y) +$$
$$G(X + 1, Y)\varepsilon_x(1 - \varepsilon_y) +$$
$$G(X, Y + 1)(1 - \varepsilon_y)\varepsilon_y +$$
$$G(X + 1, Y + 1)\varepsilon_x\varepsilon_y$$

[Mathematical expression 9]

Alternatively, instead of the linear interpolation, other interpolation methods such as the bicubic interpolation may be employed.

Alternatively, in case the device characteristics that the strains "δx", "δy" are sufficiently small are appreciated, the following mathematical expression that is an expression which performs the approximate calculation to the first term by carrying out the Taylor expansion may be employed.

$$G(x-\delta_x, y-\delta_y) = G(x,y) - G_x(x)\delta_x - G_y(x)\delta_y$$

[Mathematical expression 10]

In this mathematical expression, "Gx", "Gy" are the differential with respect to x, the differential with respect to y of "G", respectively. As the value of the differential, the value of the Sobel filter may be used.

In estimating the strain parameters, instead of minimizing all the "K−1" pieces of variables or ξk (k=1, . . . , K−1), there may be employed a method of setting a natural number "K'" which is equal to or less than "K−1", and fixing ξk with respect to "k" which is larger than "K'" to "0", and setting only "K'" pieces of ξk with respect to "k" which are equal to or less than "K'" to variables to minimize those variables. The "K'" is set up for each observation image or reference image. For example, the differential values of the observation image and reference image are calculated by the Sobel filter, and the number of pixels whose differential value is equal to or more than a predetermined threshold value is calculated, and the minimum value of "K−1" and the number of pixels is set to "K'". In this way, in estimating only "K'" pieces of parameters which are equal to or less than "K−1", there can be brought about a merit that, with respect to a paired observation image and reference image in which there are many even regions and estimating the strain is prone to be unstable, parameters to be estimated are reduced to realize stable estimation.

The strained image forming means 23 is a means that obtains the strain of the observation image R (x, y) using the strain formulation coefficients from the strain parameters obtained in the strain estimation means, and strains the reference image using the image strain amounts δx (x, y), δy (x, y).

In straining the reference image, with respect to all the "x" and "y", the value of the G (x−δx, y−δy) is obtained by the linear interpolation, and thus obtained G (x−δx, y−δy) is replaced with the G (x, y).

In obtaining the G (x−δx, y−δy), instead of the linear interpolation, other interpolation methods such as the bicubic interpolation may be employed.

Alternatively, in case the strains are small, an expression which performs the approximate calculation to the first term by carrying out the Taylor expansion may be employed.

The image comparison means 24 compares the observation image R (x, y) which is obtained in the observation image input means 11 with the reference image G (x, y) which is strained by the strained image forming means 23, and determines to set positions where the difference of the two images is large to defects. Specifically, for example, using a predetermined constant "T", regions satisfying the following mathematical expression can be set to defects.

$$|R(x,y) - G(x,y)| > T$$

[Mathematical expression 11]

Alternatively, defects can be determined using the methods disclosed in the Patent Document 3 or Patent Document 4.

Figure 2:
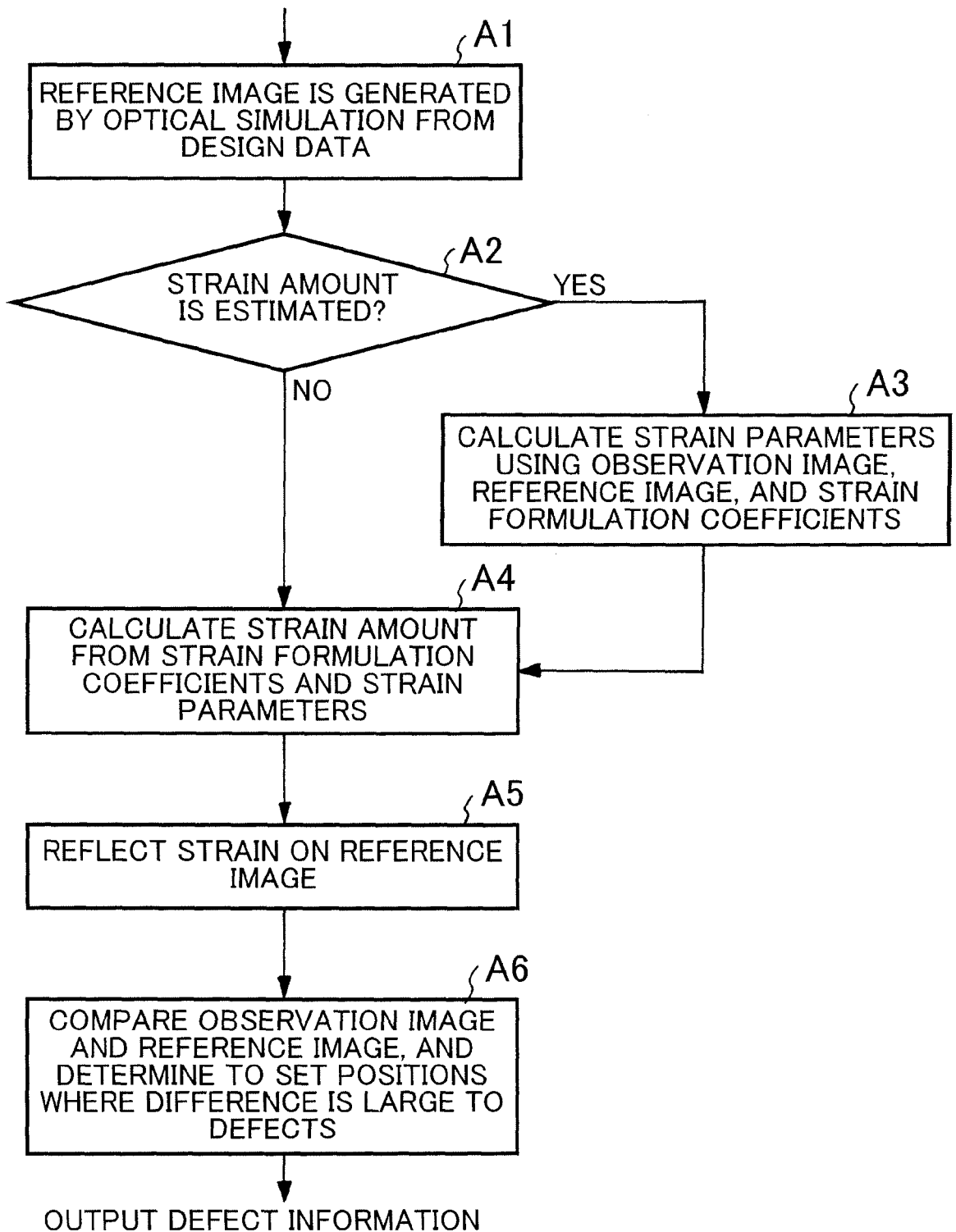
FIG. 2 shows a flowchart indicative of the performance of the best mode of the first embodiment.

Next, the performance of the best mode of the present invention will be described below in detail with reference to FIG. 1 and FIG. 2.

From the observation image input means 11 and design data input means 12 of the input device 1, an observation image of a mask to be examined and design data of a mask to be examined are input, respectively.

Firstly, in the optical simulation execution means 21, from the design data sent from the design data input means 12, the reference image G (x, y) is generated by performing the optical simulation (step A1).

Next, it is judged whether or not the strain amount is estimated using the observation image sent from the observation image input means 11 and the reference image obtained by the optical simulation execution means 21 (step A2). For example, in case it is determined to learn the strain parameters every time the mask is examined since it is anticipated that the variation per hour of the image obtention system is large and the manner of strain of the observation image is changed, the determination in step A2 is "Yes" consistently.

In case the user determines that the elapsed time from the time point of defect examination of previous time to the time point of defect examination of this time is sufficiently short as compared with the variation per hour of the image obtention system, as the determination in step A2, "No" may be selected.

Alternatively, there may be configured a system in which "No" is compulsorily selected in step A2 without the determination of the user in case the elapsed time is equal to or less than a predetermined threshold value which is give in advance. Otherwise, in case the image obtention system is significantly stable, except that the determination is "Yes" at the first time, "No" may be consistently selected in step A2 when the defect examination is carried out. In this way, increasing the number of times of selecting "No" brings about a merit that the processing can be speeded up.

In case "Yes" is selected in step A2, the strain amount estimation means 22 calculates the strain parameters using the observation image sent from the observation image input means 11, the reference image obtained in the optical simulation execution means 21, and the strain formulation coefficients stored in the strain formulation coefficient storage unit 31, and stores thus calculated strain parameters in the strain parameter storage unit 32 (step A3). At this time, comparing the strain parameters with the strain parameters that have been stored in the strain parameter storage unit 32 in advance, in case the change of the estimation value is equal to or more than a predetermined threshold value that has been given in advance, the change is equal to or more than the strain change due to the variation per hour, and it can be determined that the mask which is being observed currently is abnormal.

In case "No" is selected in step A2, or in case "Yes" is selected in step A2 and the processing of step A3 is executed, the strained image forming means 23 calculates the strain amount of the observation image from the strain parameters stored in the strain parameter storage unit 32 using the strain formulation coefficients stored in the strain formulation coefficient storage unit 31 (step A4).

Furthermore, the strained image forming means 23 strains the reference image by the strain amount (step A5).

The reference image formed by the strained image forming means 23 is supplied to the image comparison means 24. The image comparison means 24 compares the observation image sent from the observation image input means 11 with the reference image supplied from the strained image forming means 23, and determines to set positions where the difference is large to defects (step A6).

In this embodiment, the strain of an observation image which is raised at the time of obtaining the image is estimated from the image information, and a reference image is strained by the strain amount. Accordingly, defect examination with high accuracy can be realized.

Next, the best mode of the second embodiment according to the present invention will be described below in detail with reference to drawings.

Figure 6:
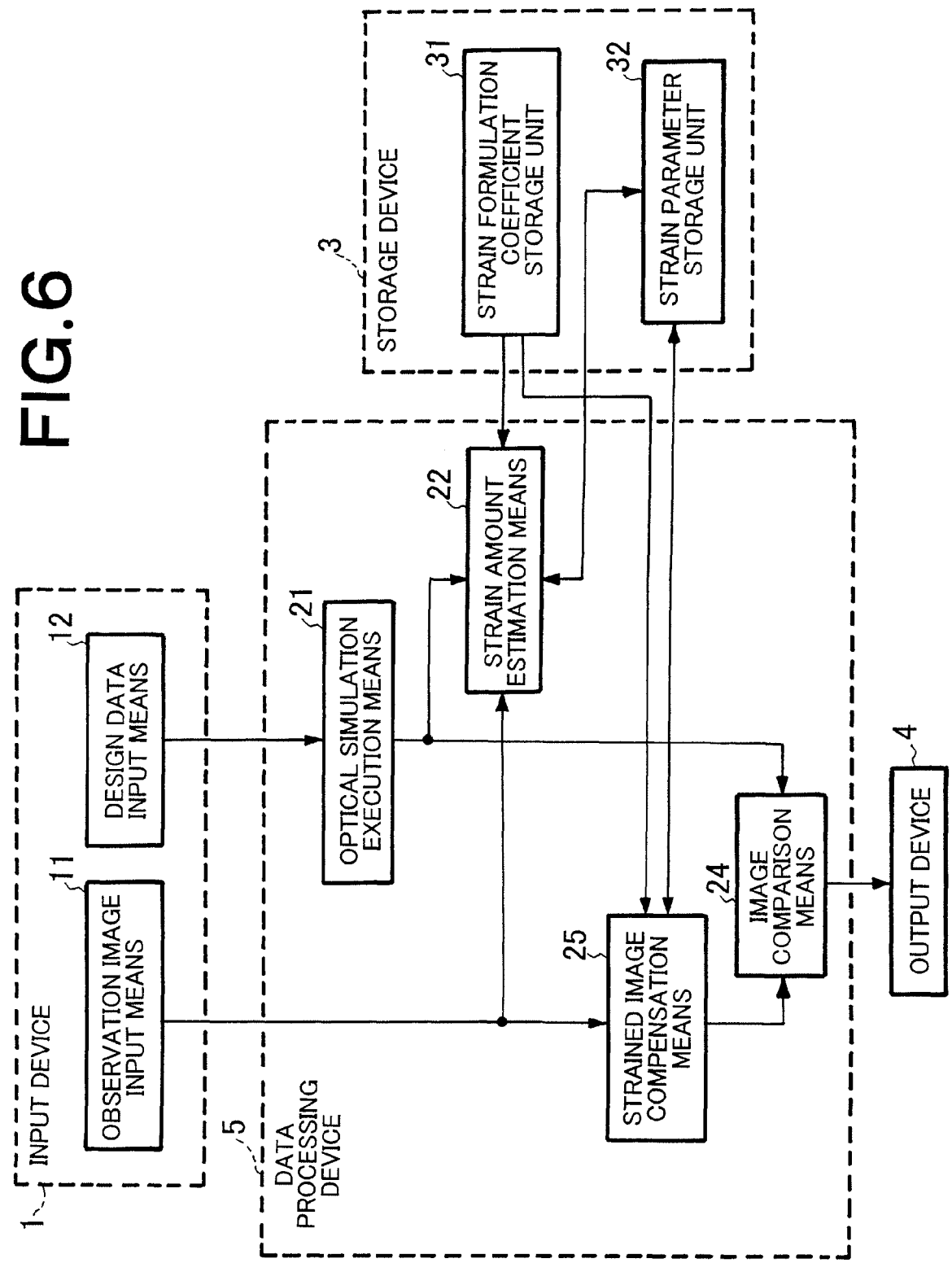
FIG. 6 shows a block diagram indicative of the configuration of the best mode of the second embodiment according to the present invention.

Referring to FIG. 6, the best mode of the second embodiment according to the present invention is different from that of the first embodiment shown in FIG. 1 in that, in a data learning device 5 which corresponds to the data processing device 2, the strained image forming means 23 is excluded and a strained image compensation means 25 is included instead.

The strained image compensation means 25 is a means that obtains the strain amount of the observation image R (x, y) using the strain formulation coefficients from the strain parameters obtained in the strain amount estimation means 22, and compensates the strain of the observation image using the image strain amounts δx (x, y), δy (x, y).

In compensating the strain, for example, R (x+δx, y+δy) is obtained by the linear interpolation, and thus obtained R (x+δx, y+δy) is replaced with the R (x, y).

In obtaining the R (x+δx, y+δy), instead of the linear interpolation, other interpolation methods such as the bicubic interpolation may be employed.

Alternatively, in case the strain is sufficiently small, an expression which performs the approximate calculation to the first term by carrying out the Taylor expansion may be employed.

Next, the entire performance of the embodiment will be described below in detail with reference to FIG. 6 and a flowchart shown in FIG. 7.

Figure 7:
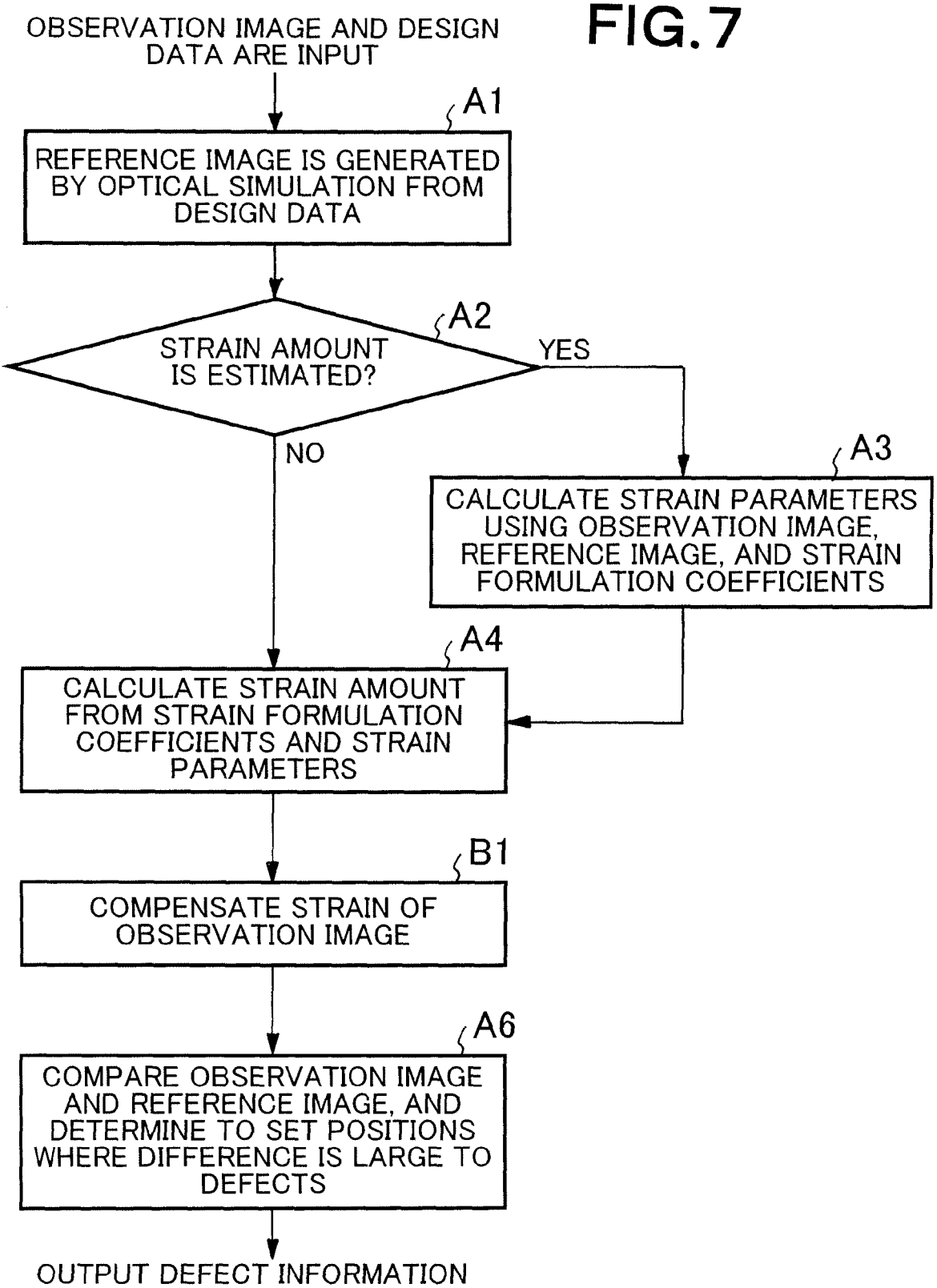
FIG. 7 shows a flowchart indicative of the performance of the best mode of the second embodiment.

Since steps A1, A2, A3, and A6 in FIG. 7 are similar to those of the first embodiment, the explanation of which is omitted.

Furthermore, step A4 is executed in the strained image compensation means 25, and the contents of which are similar to those of the first embodiment, so the explanation of which is omitted.

In this embodiment, after the strain amount of the observation image is obtained in step A4, the strained image compensation means 25 further compensates the strain existing in the observation image (step B1). Then, the observation image obtained in step B1 which has its strain compensated and the reference image obtained in the optical simulation execution means 21 are supplied to the image comparison means 24.

Next, the effect of the best mode according to the present invention will be explained.

In this best mode according to the present invention, the strain of an observation image which is raised at the time of obtaining the image is estimated from only the image information, and the strain is compensated from the observation image. Accordingly, defect examination with high accuracy can be realized.

Next, the best mode of the third embodiment according to the present invention will be described below in detail with reference to drawings.

Figure 8:
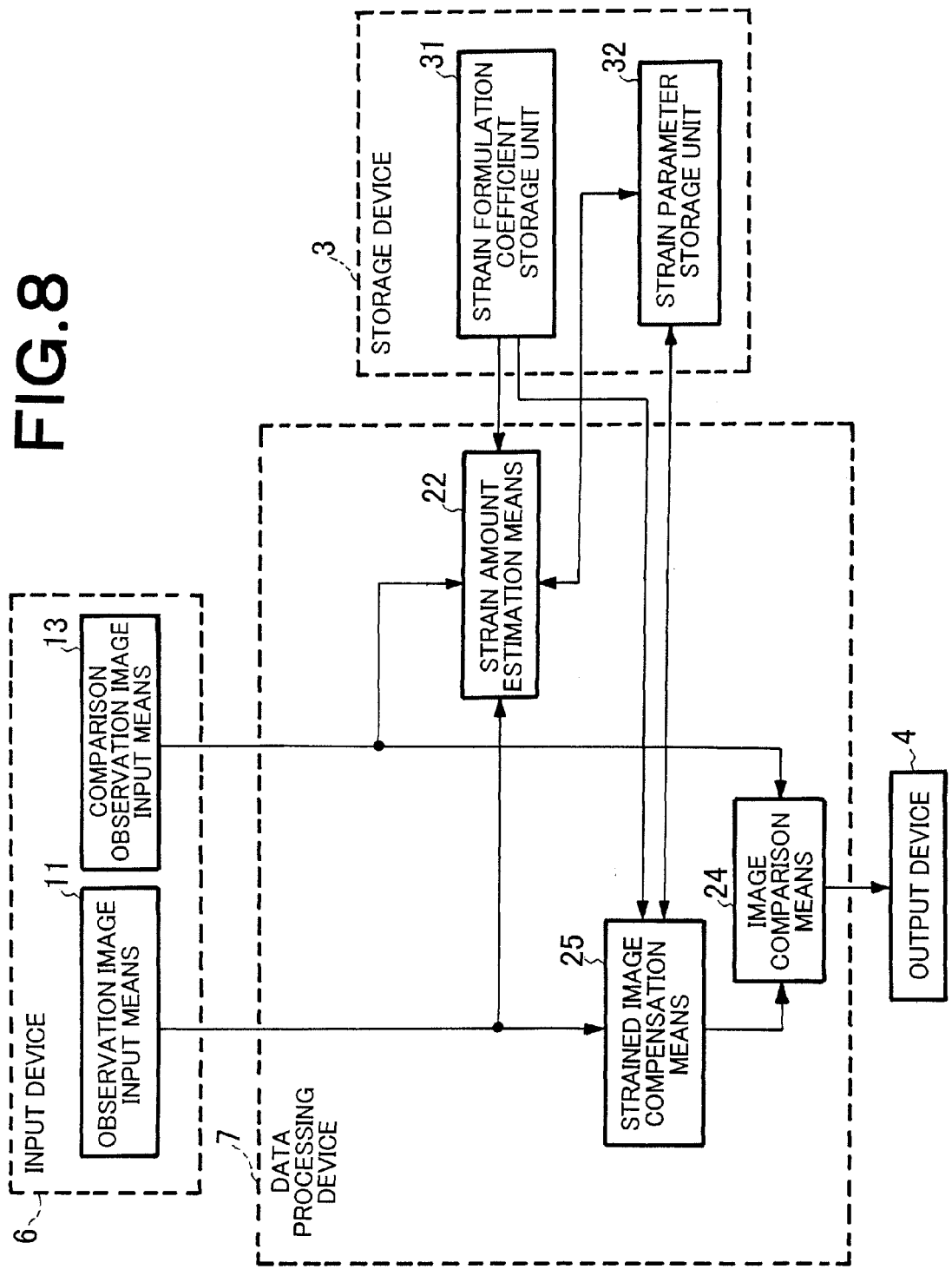
FIG. 8 shows a block diagram indicative of the configuration of the best mode of the third embodiment according to the present invention.

Referring to FIG. 8, the best mode of the third embodiment according to the present invention is different from that of the second embodiment shown in FIG. 6 in that, in an input device 6 which corresponds to the input device 1 of the second embodiment, the design data input means 12 is excluded and a comparison observation image input means 13 is included instead, and furthermore, in that, in a data learning device 7 which corresponds to the data processing device 5, the optical simulation execution means 21 is excluded.

Instead of inputting design data, the comparison observation image input means 13 inputs another observation image that is configured by the same design data as that of an observation image to be input to the observation image 11. Hereinafter, an observation image which is input by the comparison observation image input means 13 is referred to as a comparison observation image.

Next, the entire performance of the embodiment will be described below in detail with reference to FIG. 8 and a flowchart shown in FIG. 9.

Figure 9:
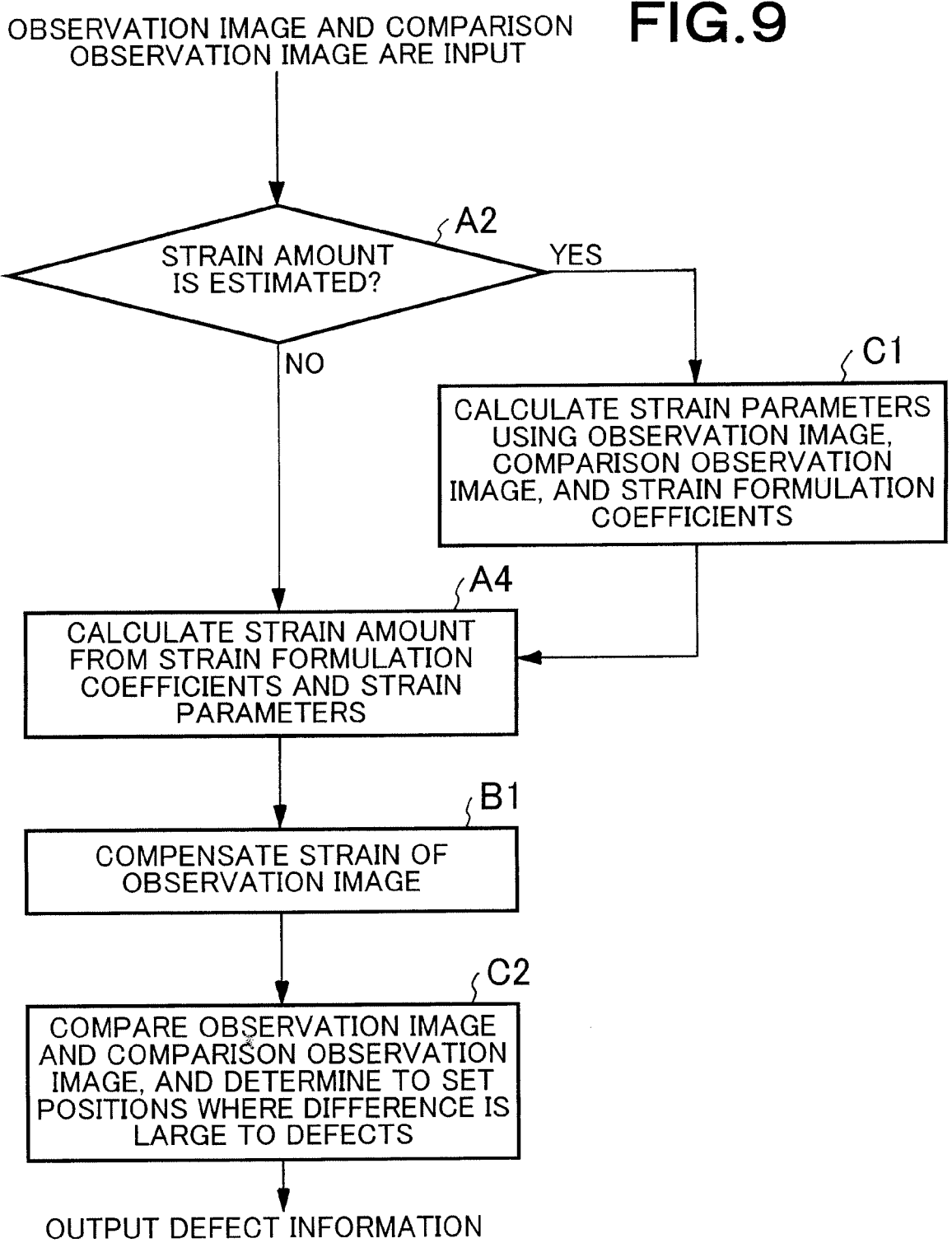
FIG. 9 shows a flowchart indicative of the performance of the best mode of the third embodiment.

Since steps A2, A4 in FIG. 9 are similar to those of the first embodiment, the explanation of which is omitted. Furthermore, when the comparison observation image is defined as R (x, y), and the reference image is replaced with the comparison observation image, step C1 is completely equal to step A3, and step C2 is completely equal to step A6.

Next, the effect of the best mode according to the present invention will be explained.

In this best mode according to the present invention, the strain of an observation image with respect to a comparison observation image which is raised at the time of obtaining the image is estimated from only the image information, and the strain is compensated from the observation image. Accordingly, defect examination with high accuracy can be realized.

Next, the best mode of the fourth embodiment according to the present invention will be described below in detail with reference to a drawing.

Figure 10:
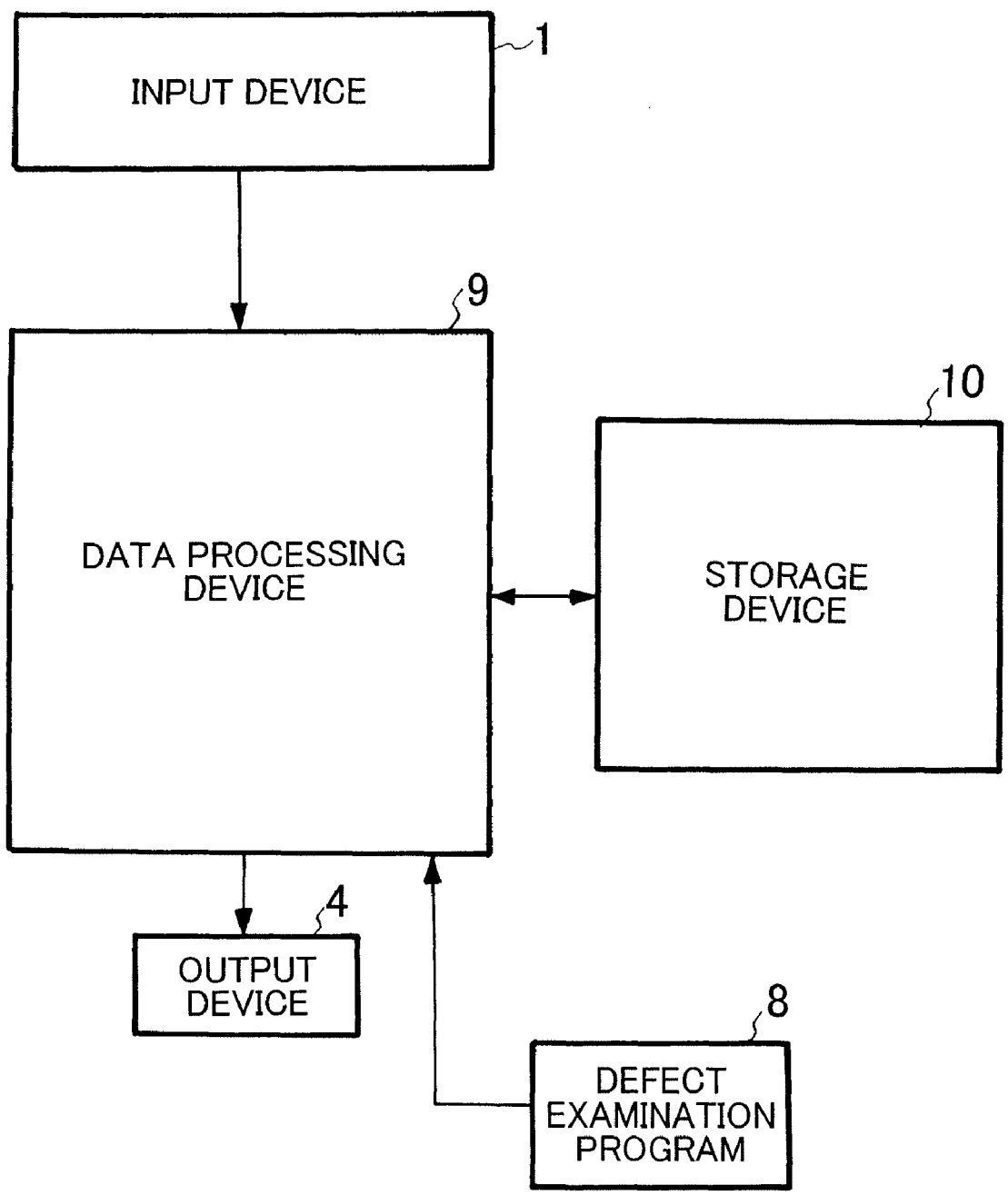
FIG. 10 shows a block diagram indicative of the configuration of the best mode of the fourth embodiment according to the present invention.

Referring to FIG. 10, similar to the best modes of the first, second, and third embodiments according to the present invention, the best mode of the fourth embodiment according to the present invention includes an input device, a data processing device, a storage device, and an output device.

A defect examination program 8 is read into a data processing device 9 to control the performance of the data processing device 9, and executes the same processing as that executed by the data processing devices 2, 5, and 7 in the first, second, and third embodiments.

Example 1

Next, referring to FIG. 2, the best mode according to the present invention will be described using a specific example. In this example, as a data processing device, a central processing unit of a personal computer is utilized. Furthermore, as a data storage device, a magnetic disk device is utilized.

Figure 11:
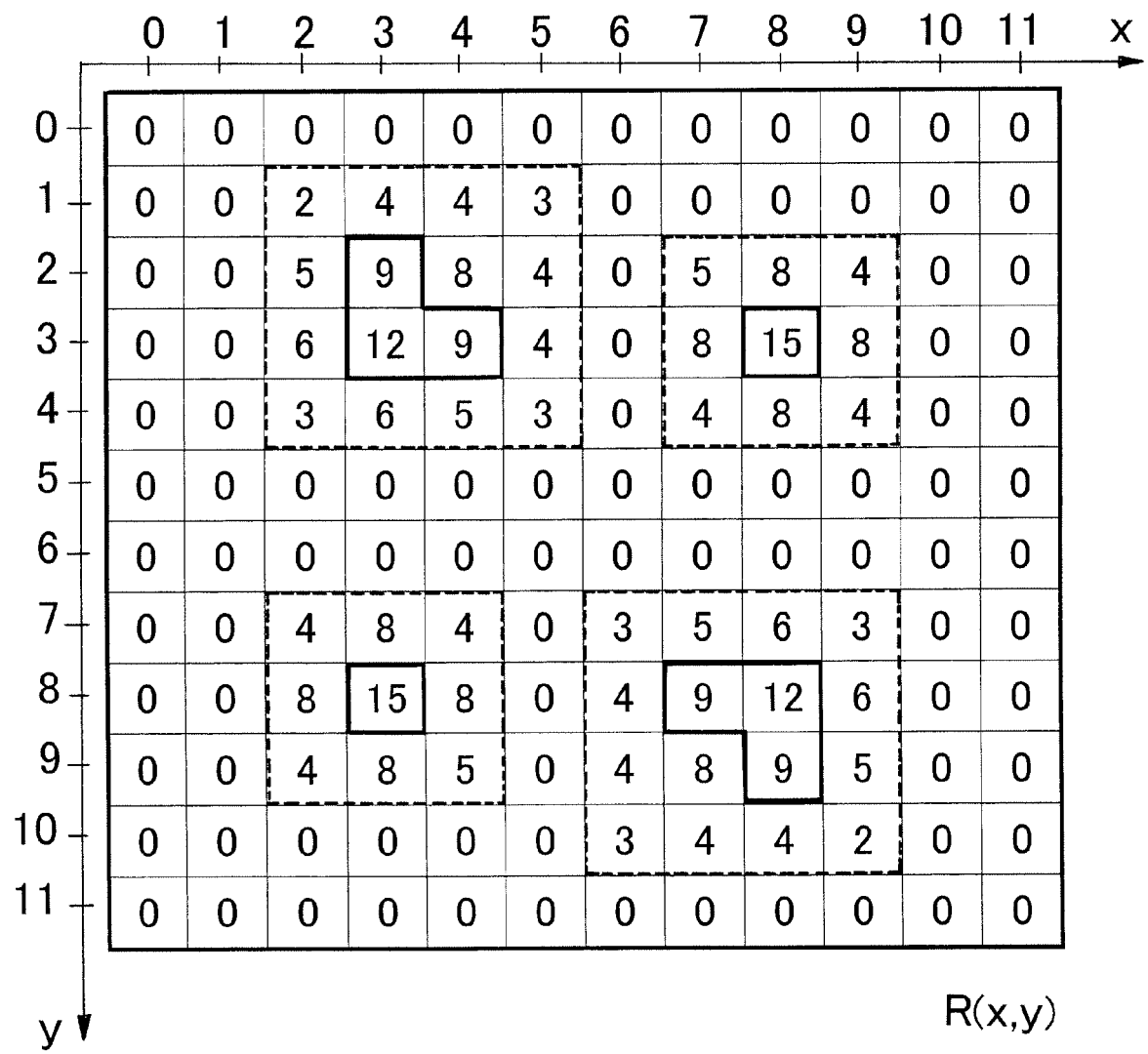
FIG. 11 shows a view of a specific example of an observation image.

It is assumed that the size of an observation image to be examined is 12 pixels in the "x" direction and 12 pixels in the "y" direction, and that the observation image is R (x, y) (where x=0, . . . , 11, y=0, . . . , 11) shown in FIG. 11.

Figure 13:
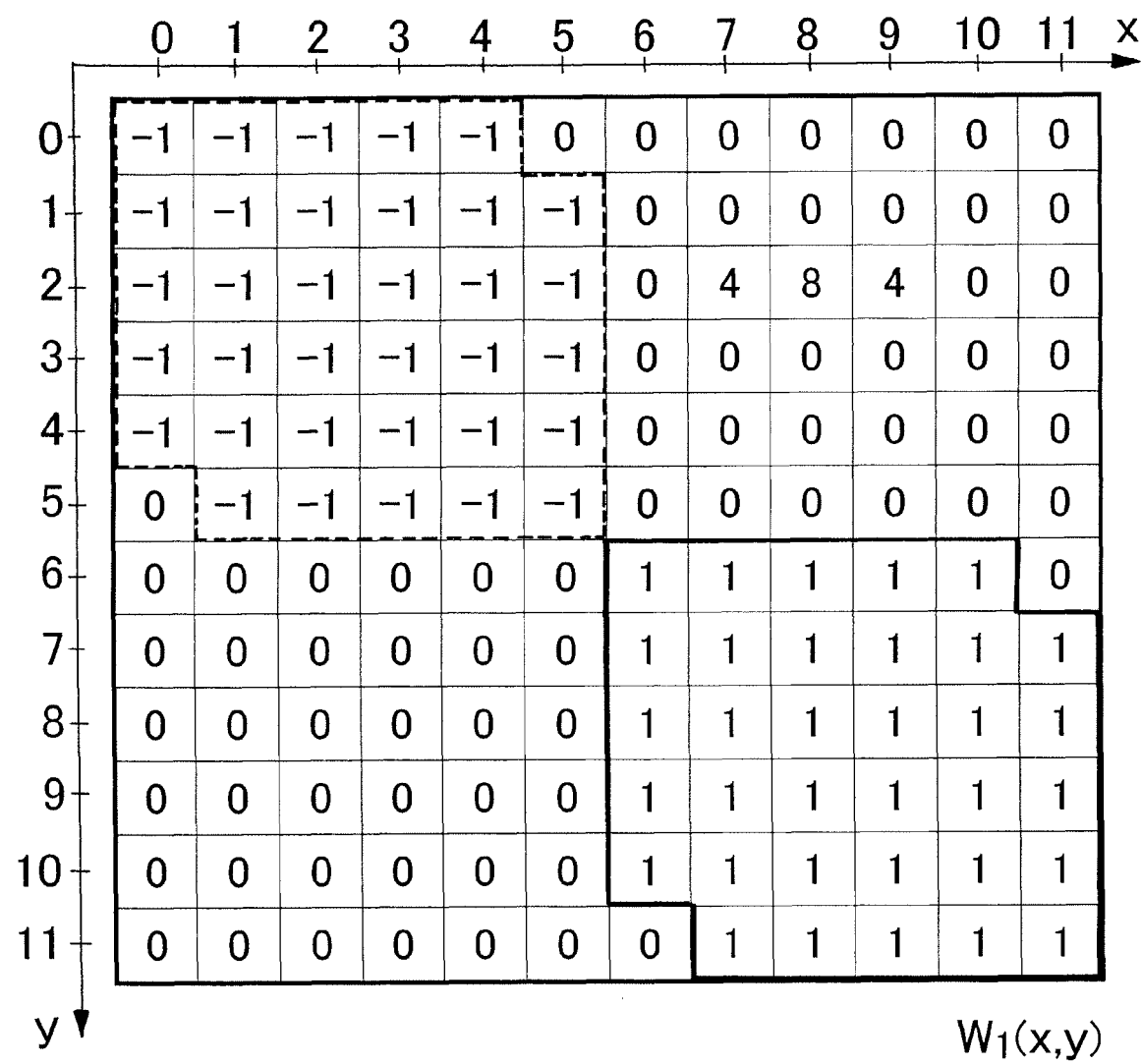
FIG. 13 shows a view of a specific example of strain formulation coefficients.
Figure 14:
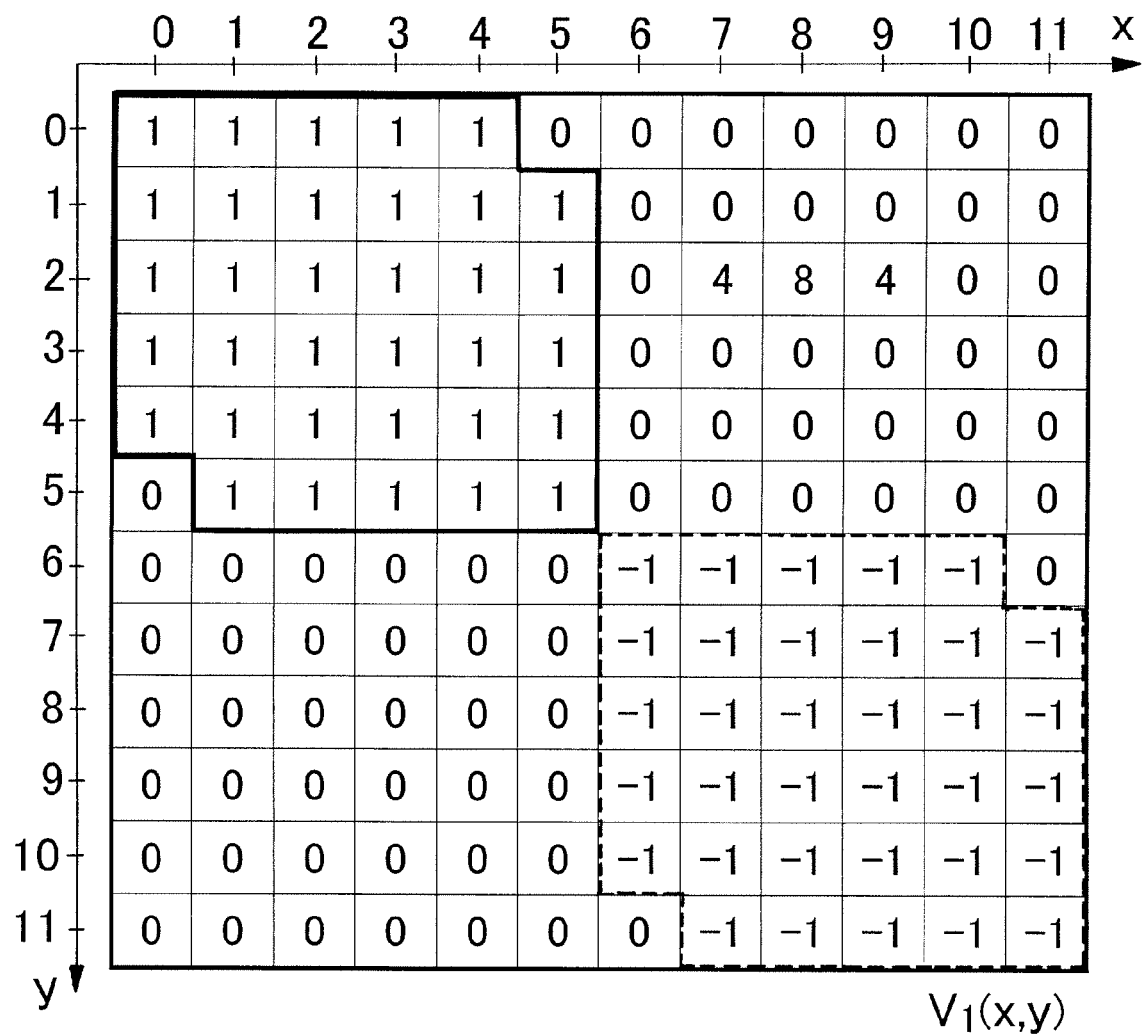
FIG. 14 shows a view of a specific example of strain formulation coefficients.

The magnetic disk device has stored therein strain formulation coefficients w1 (x, y), v1 (x, y) (where x=0, . . . , 11, y=0, . . . , 11) shown in FIG. 13 and FIG. 14, and, in addition thereto, w2 (x, y)=0, v2 (x, y)=0 (where x=0, . . . , 11, y=0, . . . , 11). That is, both the number of the strain formulation coefficients necessary in formulating the strain in the "x" direction and the number of the strain formulation coefficients necessary in formulating the strain in the "y" direction are two.

Furthermore, the strain parameter ξ1 has stored therein "0".

Firstly, design data is input to the central processing unit, and a reference image is formed by carrying out the optical simulation (step A1).

Figure 12:
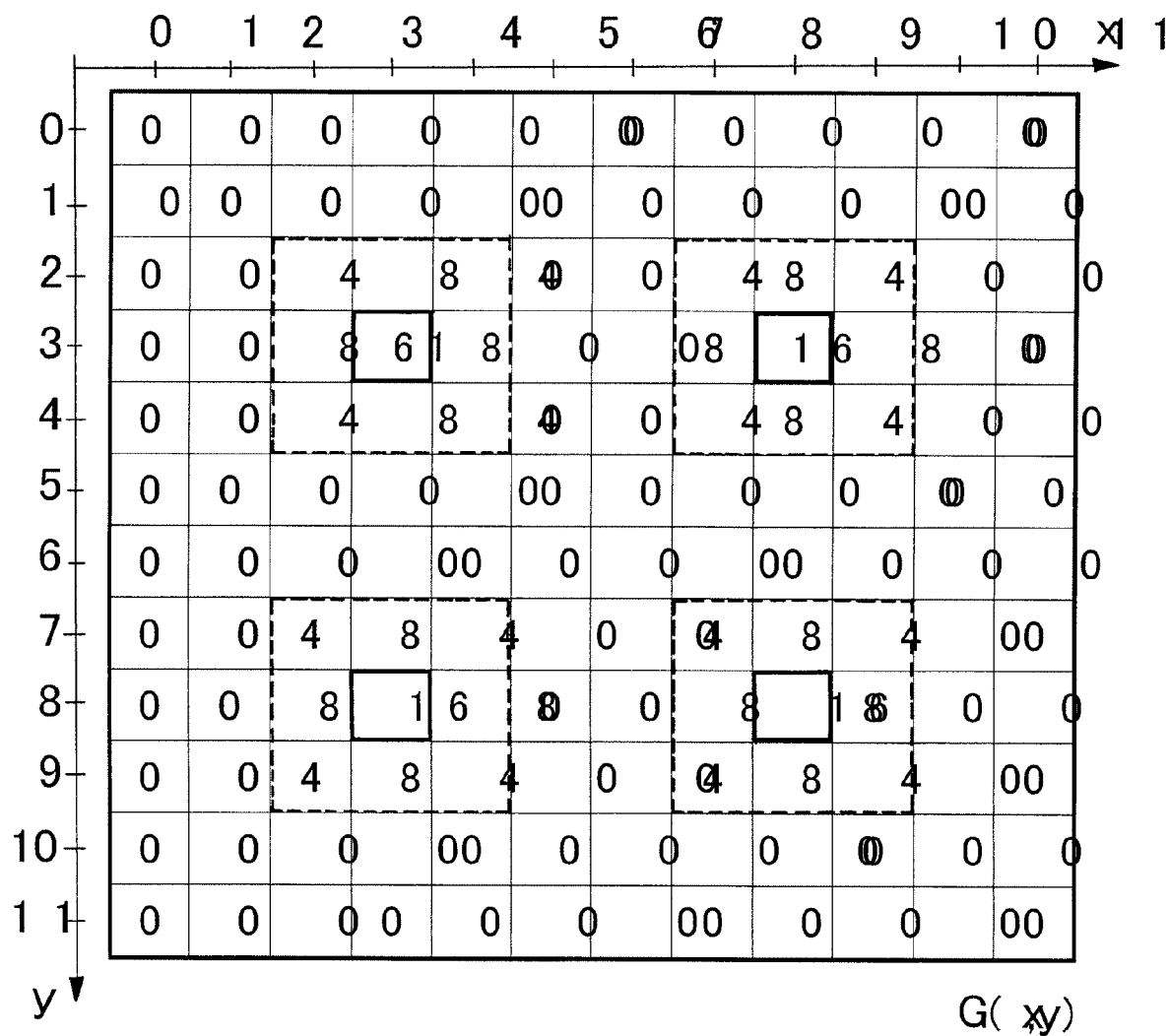
FIG. 12 shows a view of a specific example of a reference image.

FIG. 12 shows thus formed reference image G (x, y) (where x=0, . . . , 11, y=0, . . . , 11).

Next, the strain parameter ξ1 is recalculated using the reference image G (x, y), observation image R (x, y), and w1 (x, y), v1 (x, y) stored in the magnetic disk device, and thus recalculated ξ1 is stored in the magnetic disk device ("Yes" in step A2→step A3).

Specifically, the strain parameter ξ1 can be obtained by minimizing the following mathematical expression with respect to ξ1.

$$S = \sum_{x=0}^{11} \sum_{y=0}^{11} (G(x-\delta_x, y-\delta_y) - R(x, y))^2 \quad \text{[Mathematical expression 12]}$$

The δx (x, y), δy (x, y) are strain amounts at a point (x, y) of the observation image, and are expressed as follows.

$$\delta_x(x,y) = \xi_1 w_1(x,y)$$

$$\delta_y(x,y) = \xi_1 v_1(x,y) \quad \text{[Mathematical expression 13]}$$

The G (x−δx, y−δy) can be obtained by the linear interpolation.

In this embodiment, as a manner for the minimization with respect to the ξ1, there is employed a method of making the ξ1 discrete and performs the total searching. In this case, the discrete width is set to 0.5, and five ways or ξ1=−1, −0.5, 0, +0.5, +1 are examined, and a method of obtaining the ξ1 that makes "S" minimum is employed.

Figure 15:
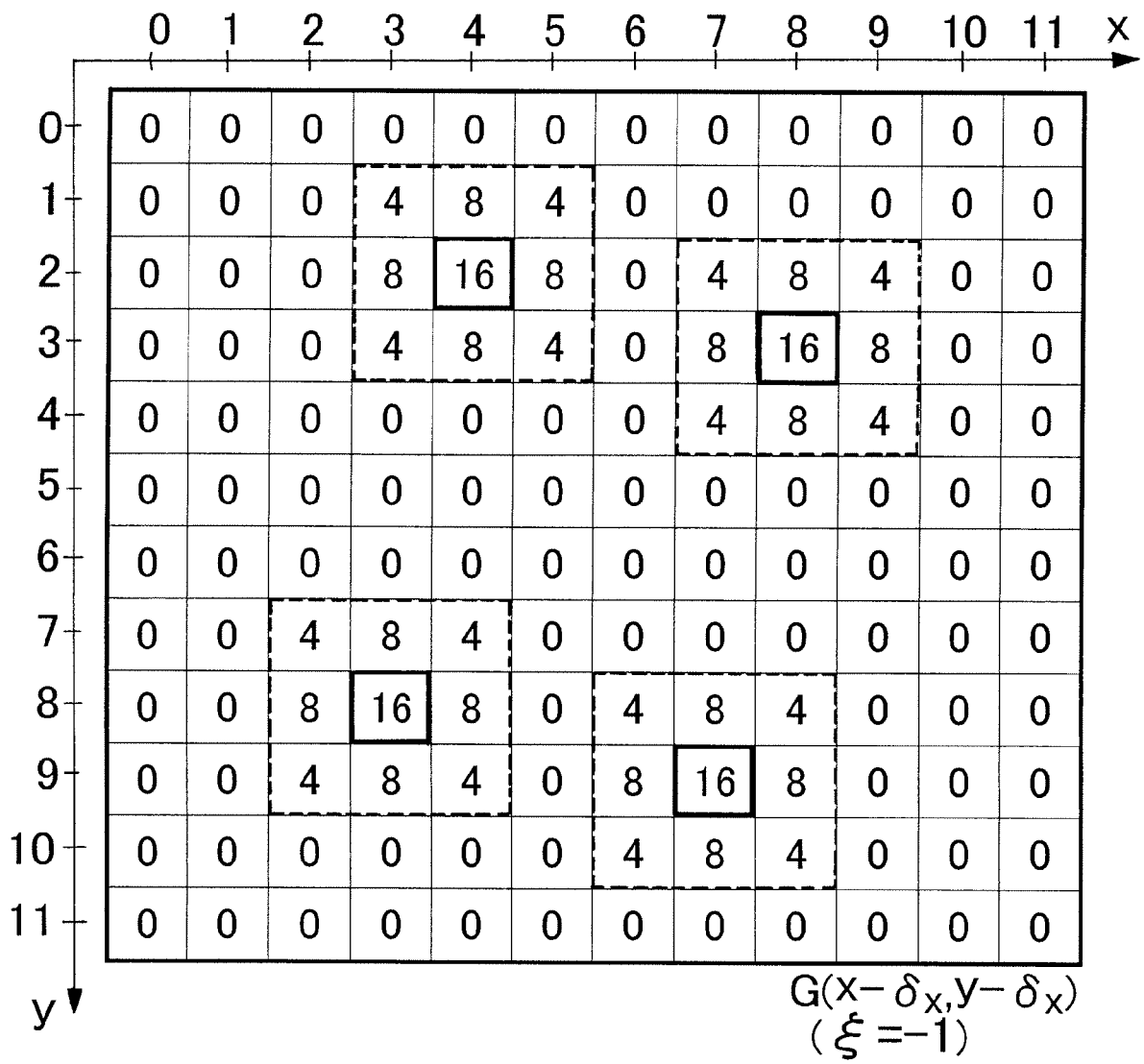
FIG. 15 shows a view of a specific example of a strained reference image.
Figure 20:
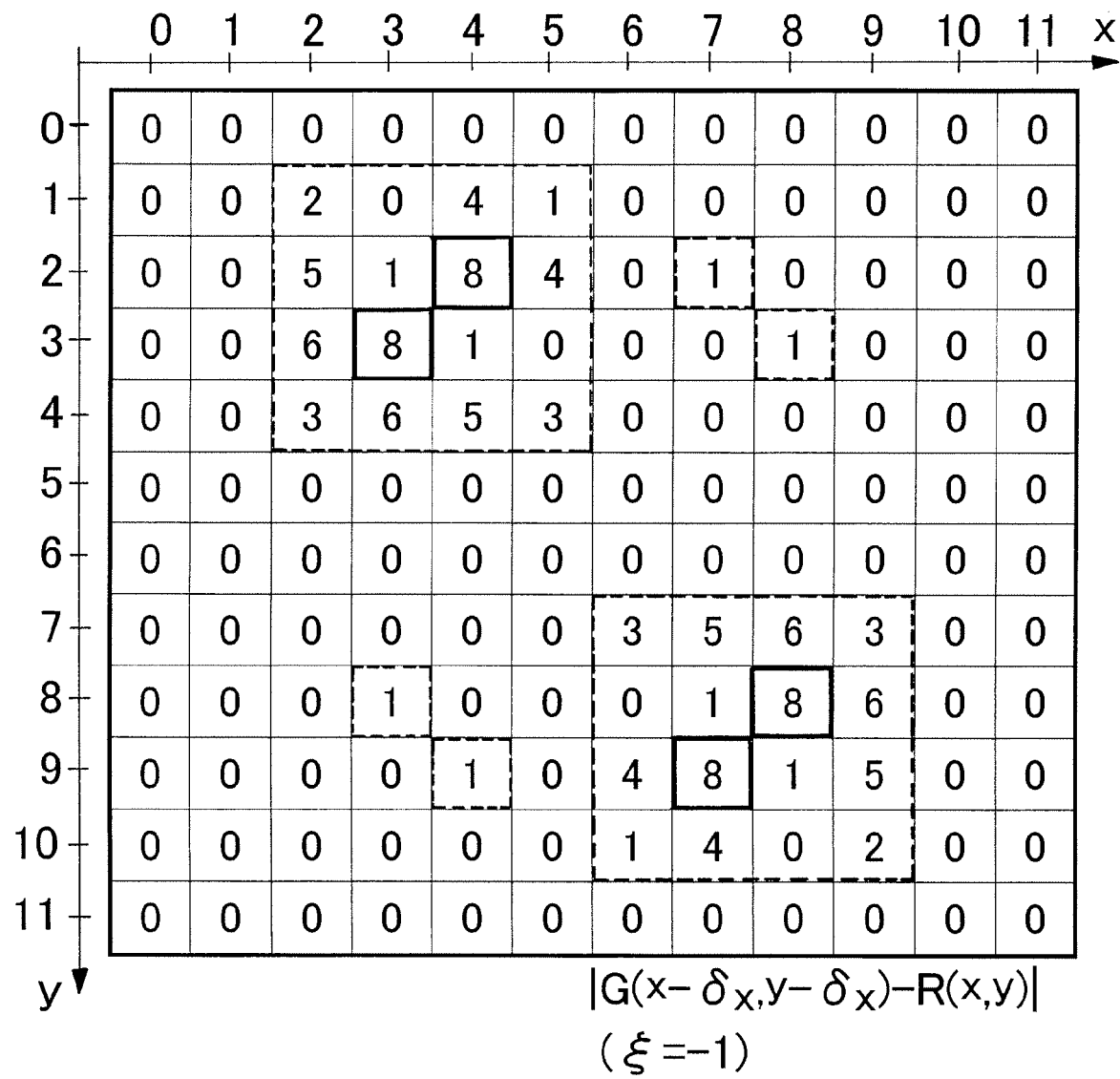
FIG. 20 shows a view of a specific example of the difference between a strained reference image and an observation image.

FIG. 15 shows the G (x−δx, y−δy) in case the ξ1=−1. FIG. 20 shows |G (x−δx, y−δy)−R (x, y)| at this time. In this case, the "S" is calculated to S=618.

Figure 16:
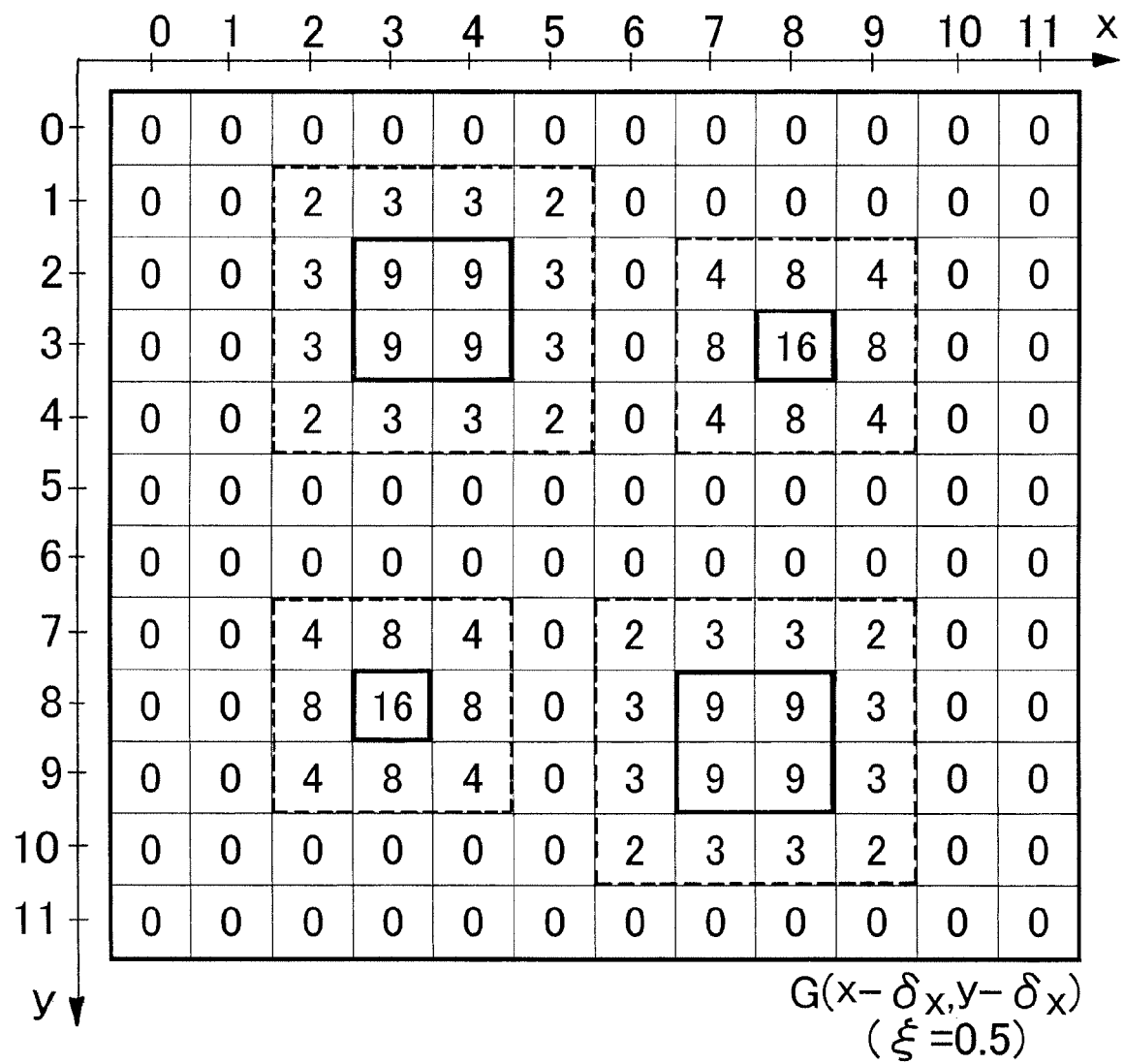
FIG. 16 shows a view of a specific example of a strained reference image.
Figure 21:
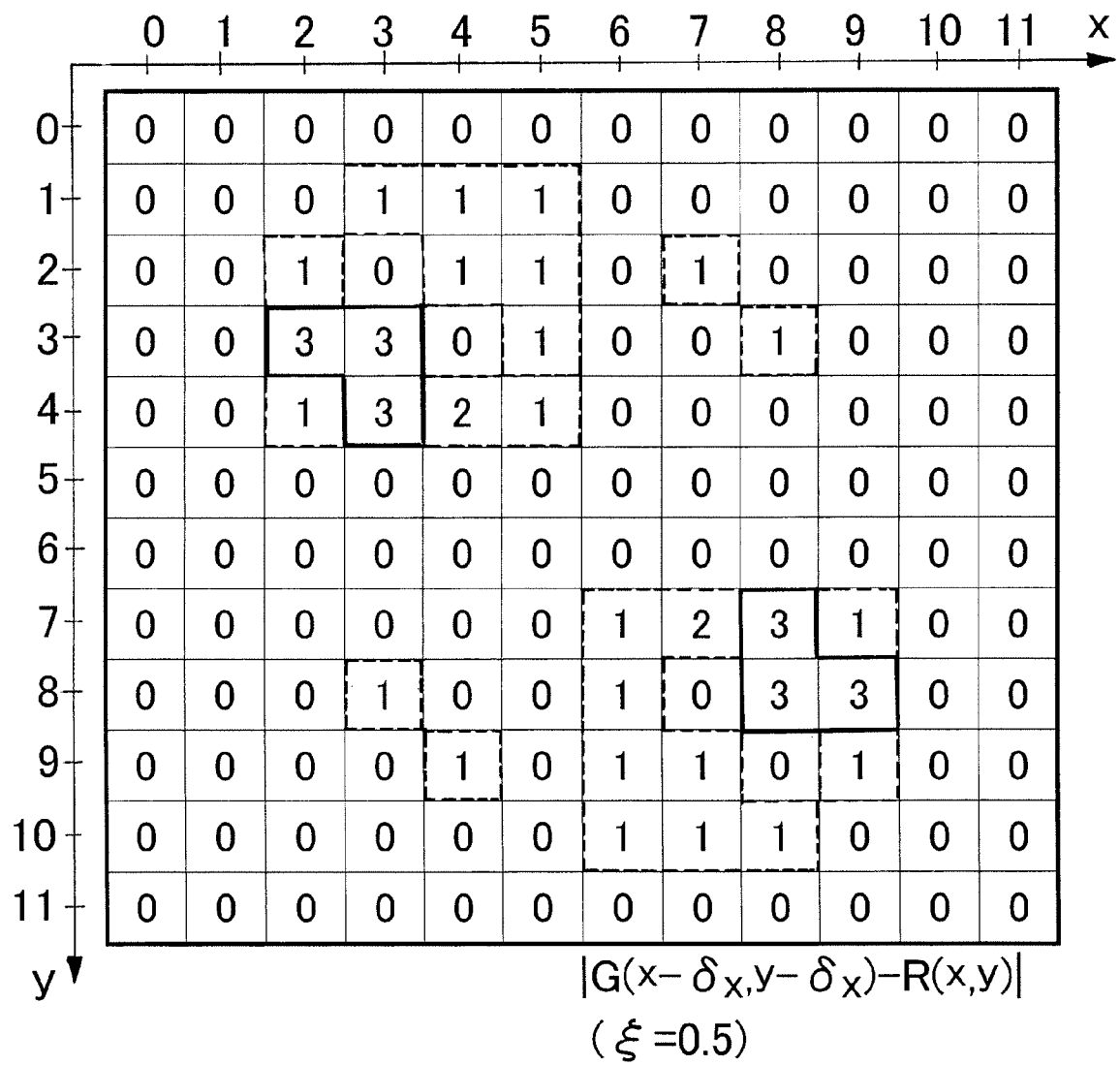
FIG. 21 shows a view of a specific example of the difference between a strained reference image and an observation image.

FIG. 16 shows the G (x−δx, y−δy) in case the ξ1=−0.5. FIG. 21 shows |G (x−δx, y−δy)−R (x, y)| at this time. In this case, the "S" is calculated to S=84.

Figure 17:
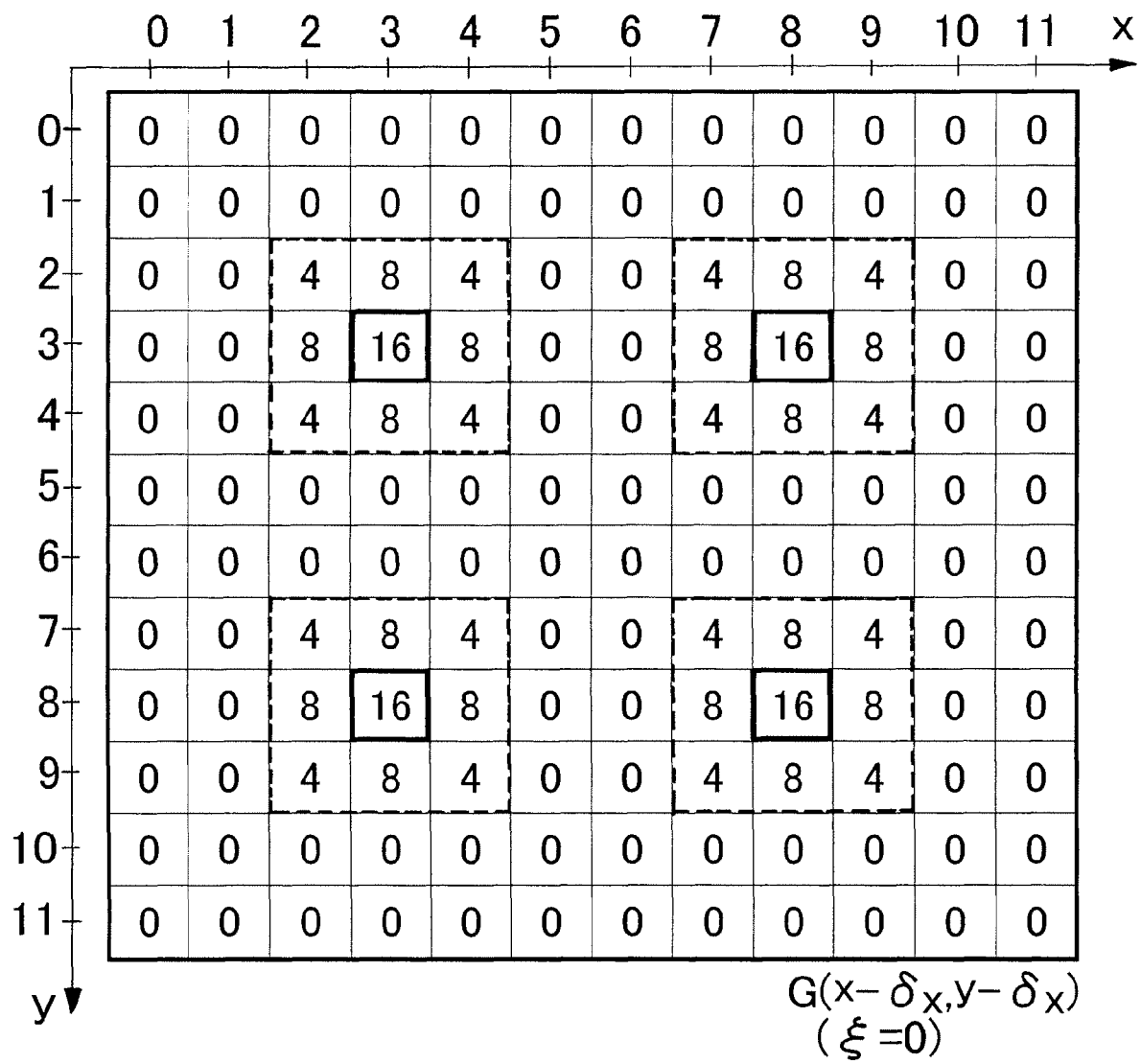
FIG. 17 shows a view of a specific example of a strained reference image.
Figure 22:
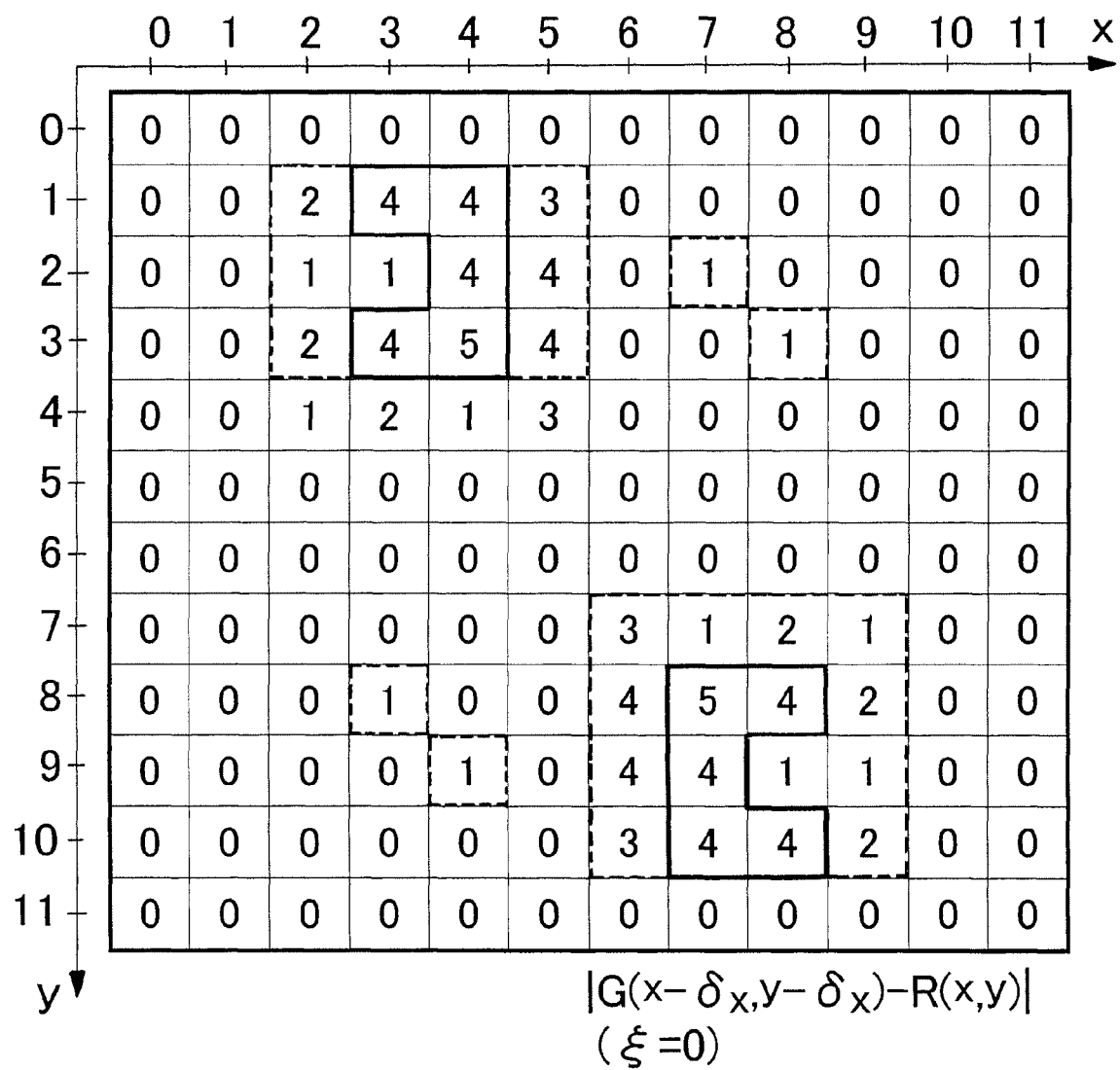
FIG. 22 shows a view of a specific example of the difference between a strained reference image and an observation image.

FIG. 17 shows the G (x−δx, y−δy) in case the ξ1=0. FIG. 22 shows |G (x−δx, y−δy)−R (x, y)| at this time. In this case, the "S" is calculated to S=314.

Figure 18:
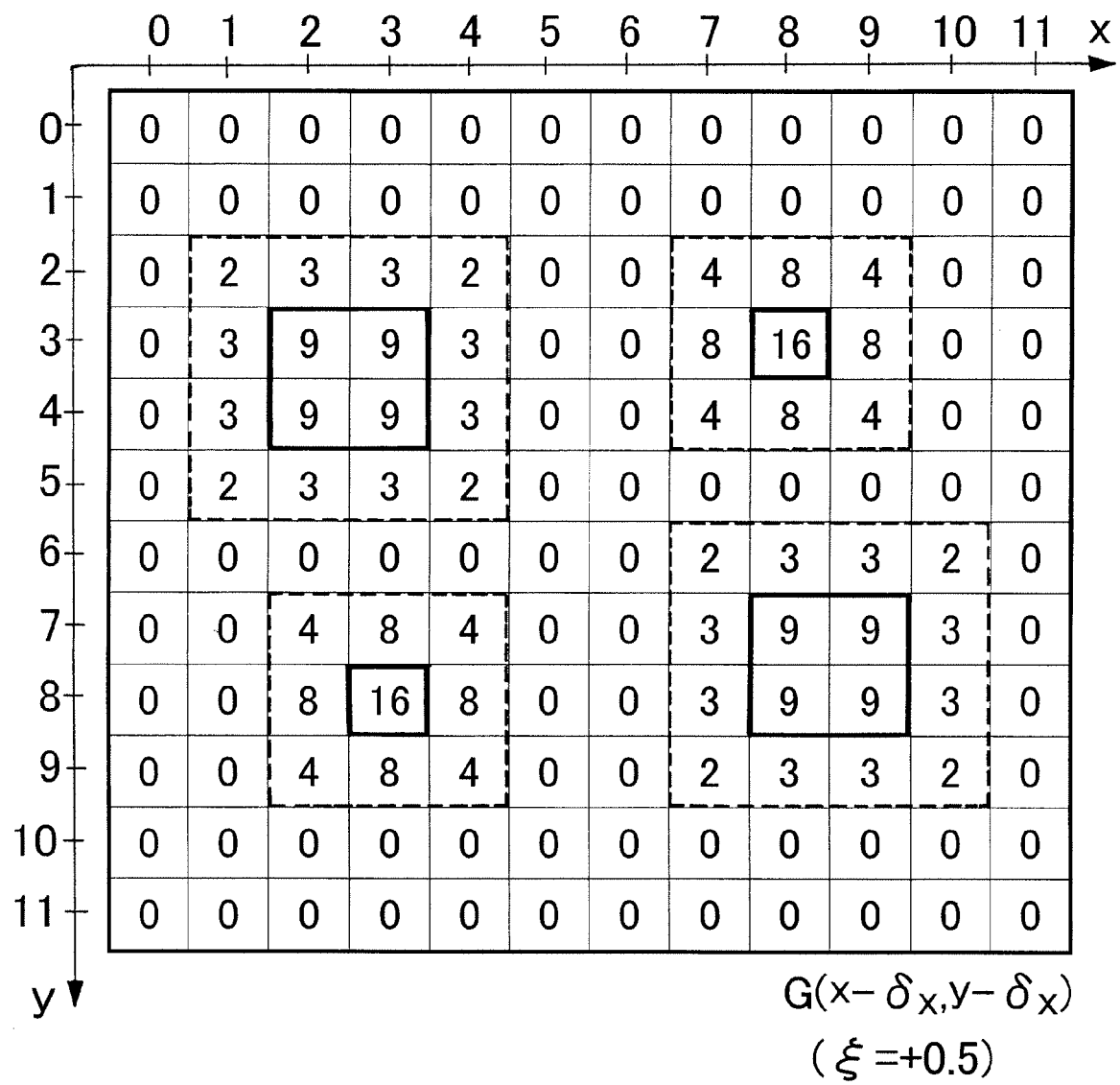
FIG. 18 shows a view of a specific example of a strained reference image.
Figure 23:
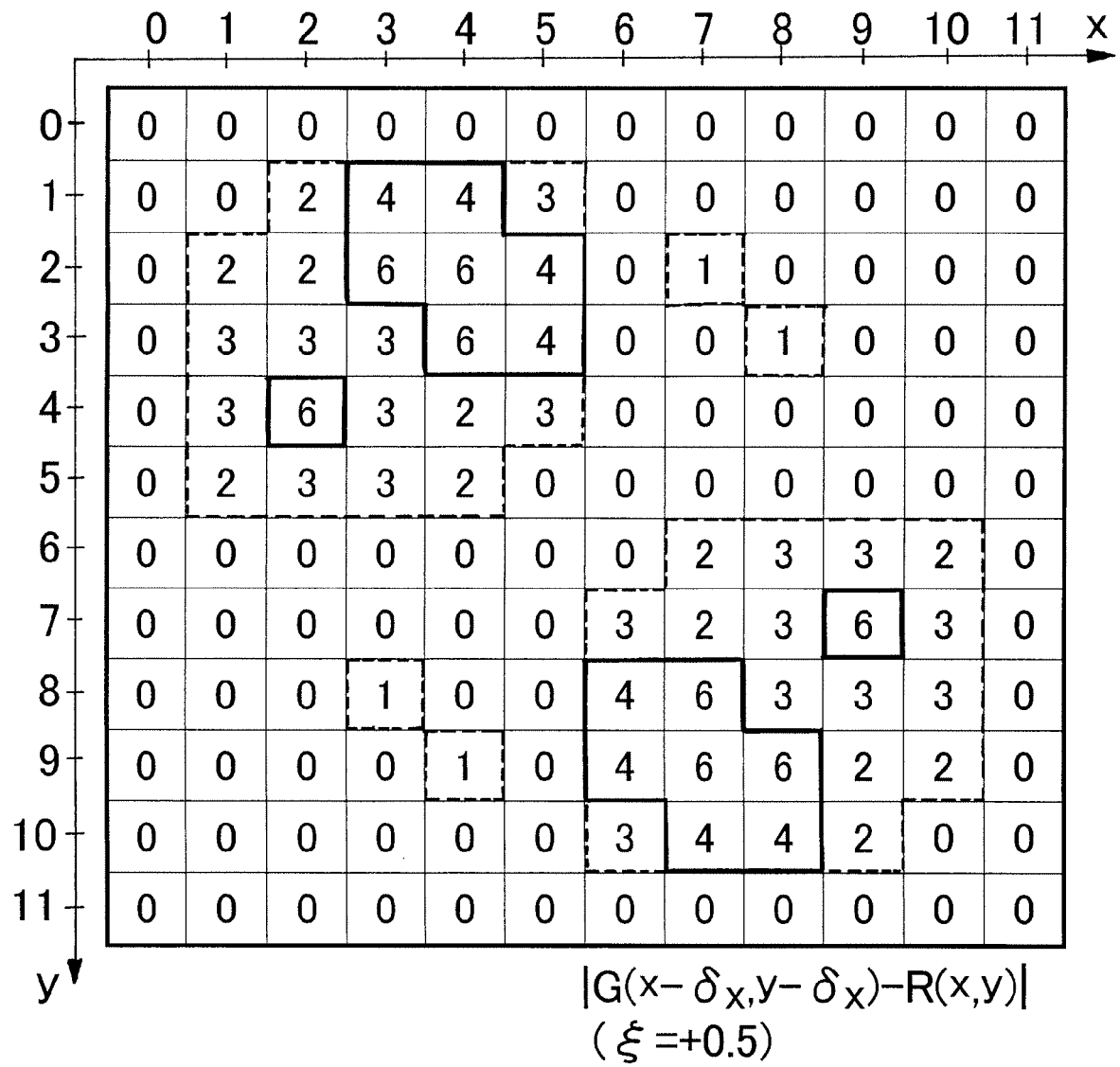
FIG. 23 shows a view of a specific example of the difference between a strained reference image and an observation image.

FIG. 18 shows the G (x−δx, y−δy) in case the ξ1=+0.5. FIG. 23 shows |G (x−δx, y−δy)−R (x, y)| at this time. In this case, the "S" is calculated to S=630.

Figure 19:
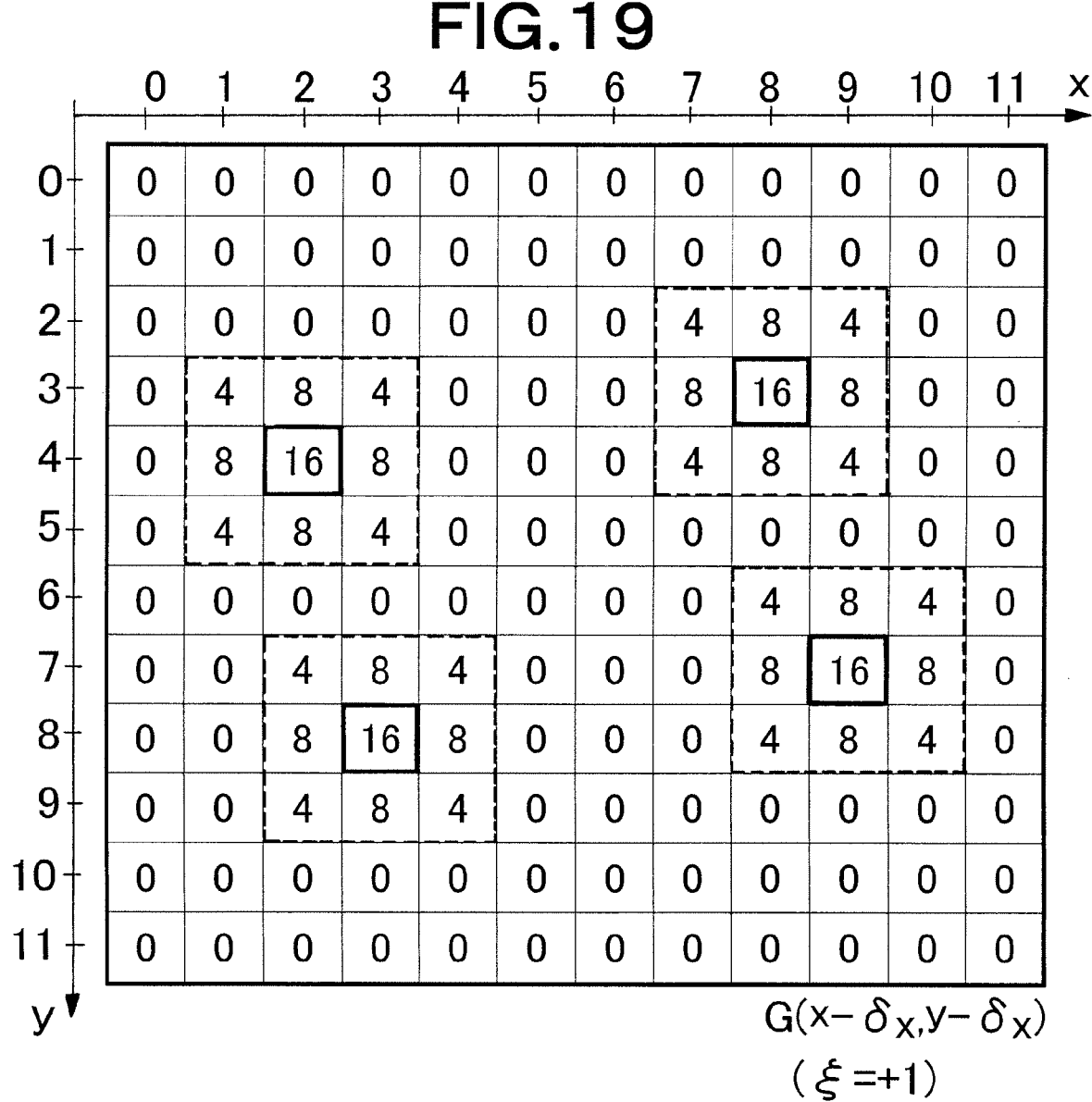
FIG. 19 shows a view of a specific example of a strained reference image.
Figure 24:
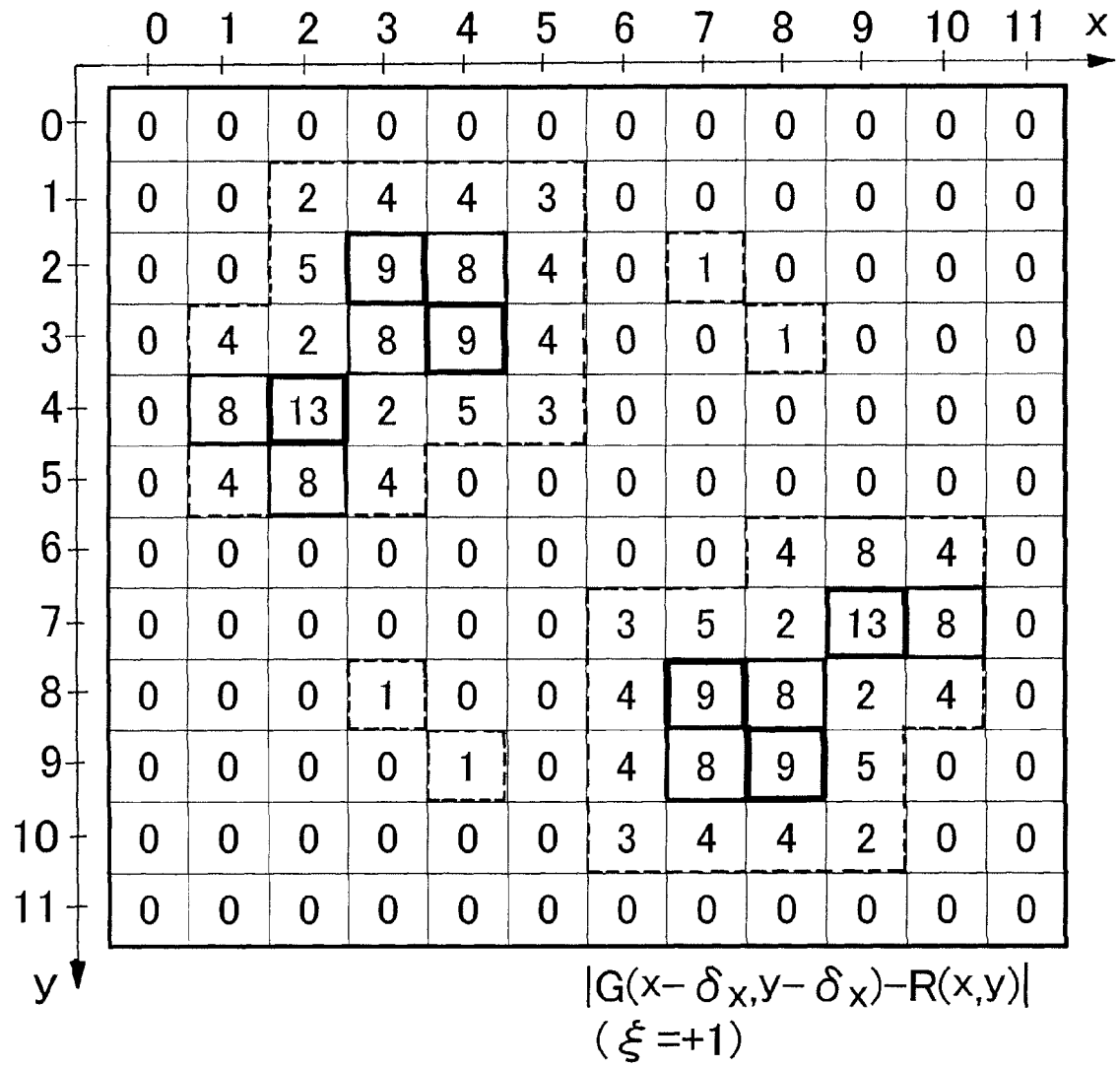
FIG. 24 shows a view of a specific example of the difference between a strained reference image and an observation image.

FIG. 19 shows the G (x−δx, y−δy) in case the ξ1=+1. FIG. 24 shows |G (x−δx, y−δy)−R (x, y)| at this time. In this case, the "S" is calculated to S=1562.

Among above-described five ways of the ξ1, the "S" comes to be minimum in case the ξ1=−0.5. Accordingly, ξ1=−0.5 is stored in the magnetic storage device.

Figure 25:
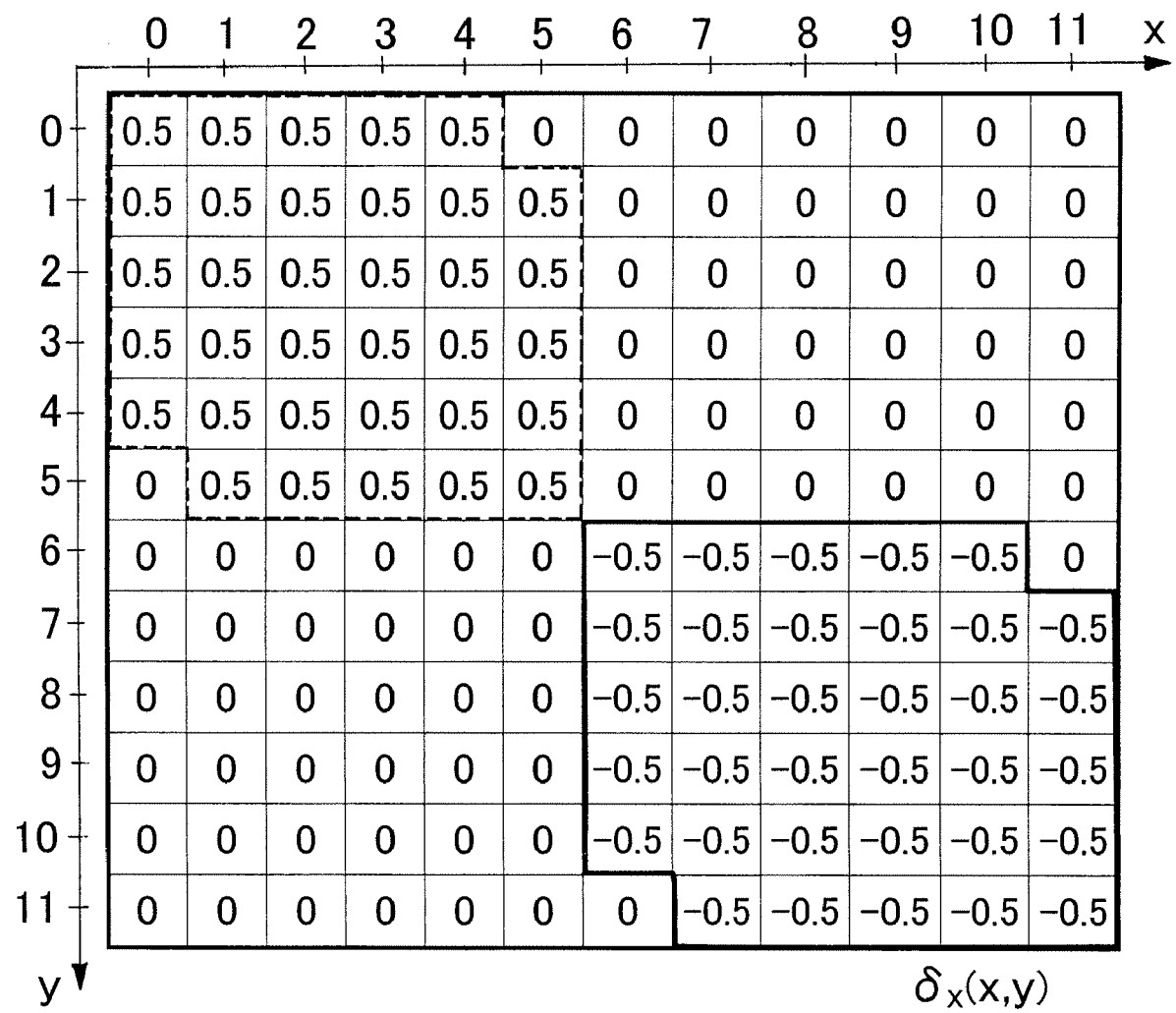
FIG. 25 shows a view of a specific example of strain amounts.
Figure 26:
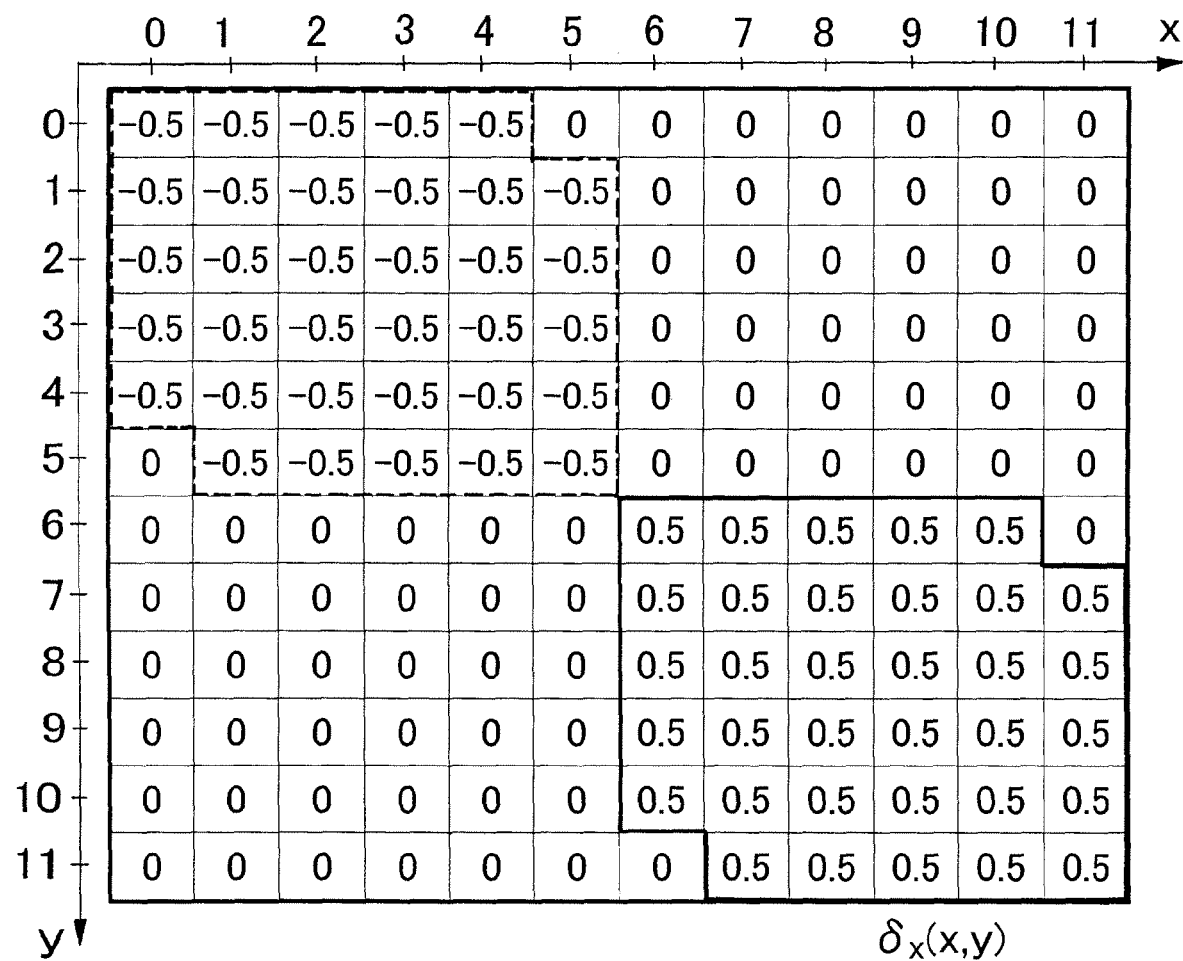
FIG. 26 shows a view of a specific example of strain amounts.

Next, a strain is given to the reference image G (x, y). The amount of strain is calculated from the w1 (x, y), v1 (x, y) and the strain parameter ξ1=−0.5 which are stored in the magnetic disk device using the mathematical expression 13. FIG. 25 and FIG. 26 show the results of the calculation (step A4).

Figure 27:
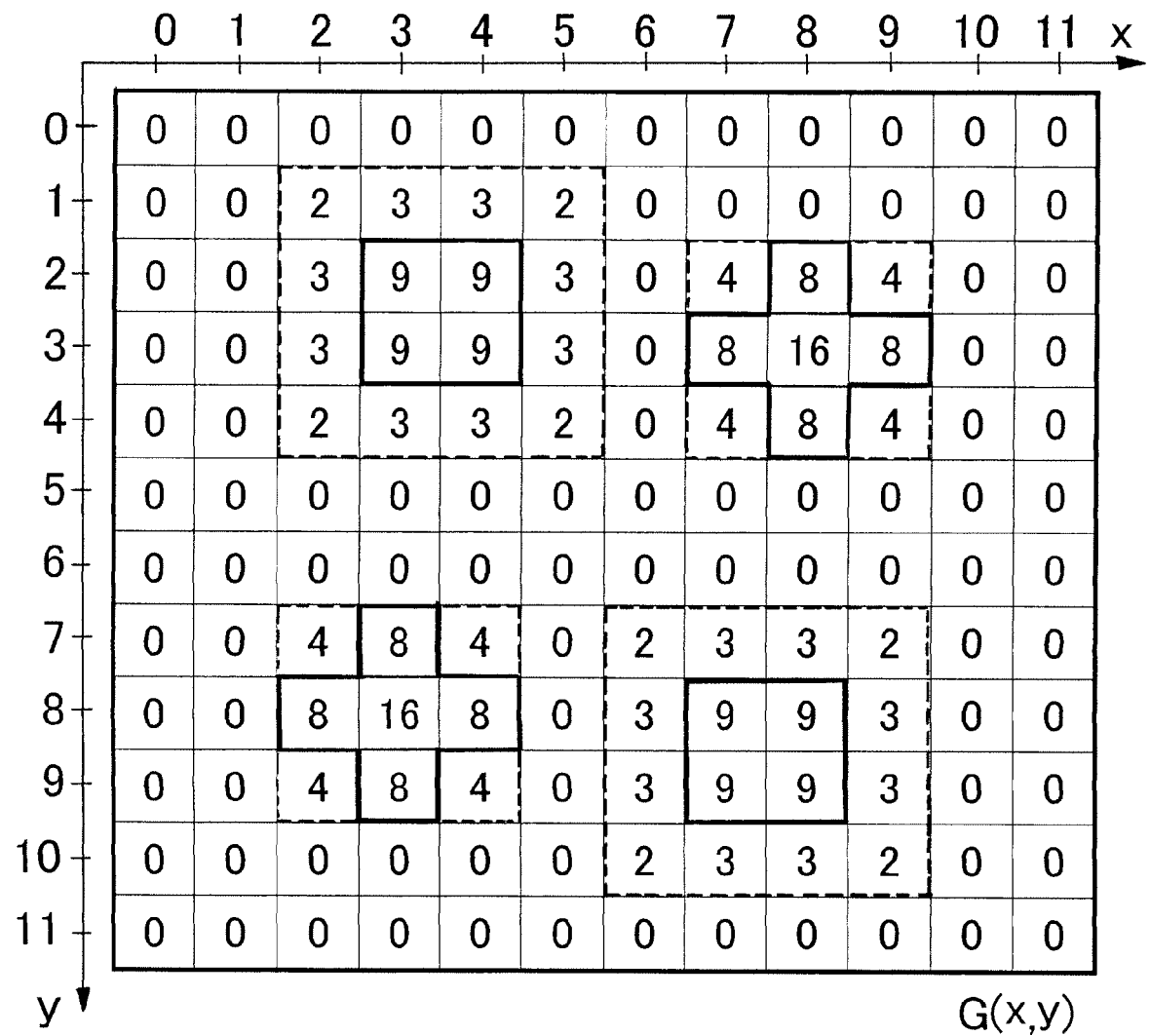
FIG. 27 shows a view of a specific example of a reference image after being strained.

The strains shown in FIG. 25 and FIG. 26 are given to the reference image (step A5). In case the linear interpolation is used as a means to give the strains, the reference image is expressed as shown in FIG. 27.

Next, the defect examination processing for an input image is performed.

After forming the reference image G (x, y), investigating the absolute value of the difference between the observation image R (x, y) and reference image G (x, y), using T=5 which has been determined in advance, it is determined that a point (x, y) satisfying the following mathematical expression is the position where a defect exists (step A6).

$$|R(x,y) - G(x,y)| > T \quad \text{[Mathematical expression 14]}$$

In this embodiment, since the maximum value of the |R (x, y)−G (x, y)| is 3, it is determined that there exists no defect.

INDUSTRIAL APPLICABILITY

According to the present invention, in examining defects of a mask which is necessary in the process of manufacturing semiconductors, the invention can be employed when examining defects by comparing an observation image which is obtained by scanning a processed pattern and a reference image which is generated using a design image corresponding to the scanned processed pattern.

The invention claimed is:

1. An apparatus for examining pattern defects comprising:
a strain amount calculation unit that compares an observation image and a reference image which is obtained from design information, or an observation image which is different from the observation image so as to estimate a strain amount;
a compensated image forming unit that forms a compensated image which is obtained by compensating one of the images which is used for the comparison using the strain amount; and
an identification unit that compares the compensated image and the other of the images which is used for the comparison so as to identify the defect of a pattern.

2. The apparatus for examining pattern defects according to claim 1, wherein estimating the strain amount is performed every time each image is examined.

3. The apparatus for examining pattern defects according to claim 1, wherein estimating the strain amount is performed every predetermined time period.

4. The apparatus for examining pattern defects according to claim 1, wherein the observation image is an image which is obtained by scanning a processed pattern using a laser beam or a charged particle beam.

5. The apparatus for examining pattern defects according to claim 1, wherein the reference image is obtained by taking the influence of an optical system at the time of obtaining the observation image into consideration with respect to pattern information included in the design information.

6. The apparatus for examining pattern defects according to claim 1, wherein the strain is expressed by a small dimension.

7. The apparatus for examining pattern defects according to claim 1, wherein the strain amount calculation unit utilizes the interpolation processing in estimating the strain amount.

8. The apparatus for examining pattern defects according to claim 7, wherein, in the interpolation processing, at least the linear interpolation or bicubic interpolation is utilized.

9. The apparatus for examining pattern defects according to claim 1, wherein the strain amount calculation unit utilizes the approximate calculation by the Taylor expansion in estimating the strain amount.

10. The apparatus for examining pattern defects according to claim 1, wherein the strain is expressed by a plurality of Gaussian distributions.

11. The apparatus for examining pattern defects according to claim 1, wherein the strain is expressed by a plurality of sinusoidal waves.

12. The apparatus for examining pattern defects according to claim 1, wherein the strain is expressed by a plurality of monomials or multinomials.

13. The apparatus for examining pattern defects according to claim 1, wherein the strain is expressed by obtaining the average value from multiple strained data which has been obtained in advance, and utilizing the average value.

14. The apparatus for examining pattern defects according to claim 13, wherein the strain is expressed by obtaining the covariance matrix from multiple strained data which has been obtained in advance, and utilizing the result of performing the principal component analysis for the covariance matrix.

15. The apparatus for examining pattern defects according to claim 14, wherein, in estimating the covariance matrix, the EM algorithm is employed.

16. The apparatus for examining pattern defects according to claim 1, wherein the strain amount calculation unit employs the method of minimizing the sum of squares of the pixel value difference between the two compared images in estimating the strain amount.

17. The apparatus for examining pattern defects according to claim 1, wherein, in the strain amount calculation unit employs the method of minimizing the total of the sum of squares of the pixel value difference between the two compared images, and the sum of function values with the value of the strain amount set to an argument in estimating the strain amount.

18. The apparatus for examining pattern defects according to claim 1, wherein the strain amount and a strain amount which has been stored in advance are compared, and it is determined that the strain amount is abnormal in case the difference is sufficiently large.

19. The apparatus for examining pattern defects according to claim 1, wherein the strain amount calculation unit variably sets up the dimension for the estimation according to the contents of the compared images in estimating the strain amount.

20. A method of examining pattern defects comprising:
a strain amount calculation step of comparing an observation image and a reference image which is obtained from design information, or an observation image which is different from the observation image so as to estimate a strain amount;
a compensated image forming step of forming a compensated image which is obtained by compensating one of the images which is used for the comparison using the strain amount; and
an identification step of comparing the compensated image and the other of the images which is used for the comparison so as to identify the defect of a pattern.

21. The method of examining pattern defects according to claim 20, wherein estimating the strain amount is performed every time each image is examined.

22. The method of examining pattern defects according to claim 20, wherein estimating the strain amount is performed every predetermined time period.

23. The method of examining pattern defects according to claim 20, wherein the observation image is an image which is obtained by scanning a processed pattern using a laser beam or a charged particle beam.

24. The method of examining pattern defects according to claim 20, wherein the reference image is obtained by taking the influence of an optical system at the time of obtaining the observation image into consideration with respect to pattern information included in the design information.

25. The method of examining pattern defects according to claim 20, wherein the strain is expressed by a small dimension.

26. The method of examining pattern defects according to claim 20, wherein the strain amount calculation step utilizes the interpolation processing in estimating the strain amount.

27. The method of examining pattern defects according to claim 26, wherein, in the interpolation processing, at least the linear interpolation or bicubic interpolation is utilized.

28. The method of examining pattern defects according to claim 20, wherein the strained image amount calculation step utilizes the approximate calculation by the Taylor expansion in estimating the strain amount.

29. The method of examining pattern defects according to claim 20, wherein the strain is expressed by a plurality of Gaussian distributions.

30. The method of examining pattern defects according to claim 20, wherein the strain is expressed by a plurality of sinusoidal waves.

31. The method of examining pattern defects according to claim 20, wherein the strain is expressed by a plurality of monomials or multinomials.

32. The method of examining pattern defects according to claim 20, wherein the strain is expressed by obtaining the average value from multiple strained data which has been obtained in advance, and utilizing the average value.

33. The method of examining pattern defects according to claim 32, wherein the strain is expressed by obtaining the covariance matrix from multiple strained data which has been obtained in advance, and utilizing the result of performing the principal component analysis for the covariance matrix.

34. The method of examining pattern defects according to claim 33, wherein, in estimating the covariance matrix, the EM algorithm is employed.

35. The method of examining pattern defects according to claim 20, wherein the strain amount calculation step employs the method of minimizing the sum of squares of the pixel value difference between the two compared images in estimating the strain amount.

36. The method of examining pattern defects according to claim 20, wherein the strain amount calculation step employs the method of minimizing the total of the sum of squares of the pixel value difference between the observation image and reference image, and the sum of function values with the value of the strain amount set to an argument in estimating the strain amount.

37. The method of examining pattern defects according to claim 20, wherein the strain amount and a strain amount which has been stored in advance are compared, and it is determined that the strain amount is abnormal in case the difference is sufficiently large.

38. The method of examining pattern defects according to claim 20, wherein the strain amount calculation step variably sets up the dimension for the estimation according to the contents of the compared images in estimating the strain amount.

39. A computer-readable recording medium having recorded therein a program that makes a computer execute a method of examining pattern defects, the method comprising:
a strain amount calculation step of comparing an observation image and a reference image which is obtained from design information, or an observation image which is different from the observation image so as to estimate a strain amount;

a compensated image forming step of forming a compensated image which is obtained by compensating one of the images which is used for the comparison using the strain amount; and an identification step of comparing the compensated image and the other of the images which is used for the comparison so as to identify the defect of a pattern.

40. The computer-readable recording medium having recorded therein a program that makes a computer execute a method of examining pattern defects according to claim 39, wherein estimating the strain amount is performed every time each image is examined.

41. The computer-readable recording medium having recorded therein a program that makes a computer execute a method of examining pattern defects according to claim 39, wherein estimating the strain amount is performed every predetermined time period.

42. The computer-readable recording medium having recorded therein a program that makes a computer execute a method of examining pattern defects according to claim 39, wherein the observation image is an image which is obtained by scanning a processed pattern using a laser beam or a charged particle beam.

43. The computer-readable recording medium having recorded therein a program that makes a computer execute a method of examining pattern defects according to claim 39, wherein the reference image is obtained by taking the influence of an optical system at the time of obtaining the observation image into consideration with respect to pattern information included in the design information.

44. The computer-readable recording medium having recorded therein a program that makes a computer execute a method of examining pattern defects according to claim 39, wherein the strain is expressed by a small dimension.

45. The computer-readable recording medium having recorded therein a program that makes a computer execute a method of examining pattern defects according to claim 39, wherein, as the strain amount calculation step utilizes the interpolation processing in estimating the strain amount.

46. The computer-readable recording medium having recorded therein a program that makes a computer execute a method of examining pattern defects according to claim 45, wherein, in the interpolation processing, at least the linear interpolation or bicubic interpolation is utilized.

47. The computer-readable recording medium having recorded therein a program that makes a computer execute a method of examining pattern defects according to claim 39, wherein the strain amount calculation step utilizes the approximate calculation by the Taylor expansion in estimating the strain amount.

48. The computer-readable recording medium having recorded therein a program that makes a computer execute a method of examining pattern defects according to claim 39, wherein the strain is expressed by a plurality of Gaussian distributions.

49. The computer-readable recording medium having recorded therein a program that makes a computer execute a method of examining pattern defects according to claim 39, wherein the strain is expressed by a plurality of sinusoidal waves.

50. The computer-readable recording medium having recorded therein a program that makes a computer execute a method of examining pattern defects according to claim 39, wherein the strain is expressed by a plurality of monomials or multinomials.

51. The computer-readable recording medium having recorded therein a program that makes a computer execute a method of examining pattern defects according to claim 39, wherein the strain is expressed by obtaining the average value from multiple strained data which has been obtained in advance, and utilizing the average value.

52. The computer-readable recording medium having recorded therein a program that makes a computer execute a method of examining pattern defects according to claim 51, wherein the strain is expressed by obtaining the covariance matrix from multiple strained data which has been obtained in advance, and utilizing the result of performing the principal component analysis for the covariance matrix.

53. The computer-readable recording medium having recorded therein a program that makes a computer execute a method of examining pattern defects according to claim 52, wherein, in estimating the covariance matrix, the EM algorithm is employed.

54. The computer-readable recording medium having recorded therein a program that makes a computer execute a method of examining pattern defects according to claim 39, wherein the strain amount calculation step employs the method of minimizing the sum of squares of the pixel value difference between the two compared images in estimating the strain amount.

55. The computer-readable recording medium having recorded therein a program that makes a computer execute a method of examining pattern defects according to claim 39, wherein the strain amount calculation step employs the method of minimizing the total of the sum of squares of the pixel value difference between the two compared images, and the sum of function values with the value of the strain amount set to an argument is employed.

56. The computer-readable recording medium having recorded therein a program that makes a computer execute a method of examining pattern defects according to claim 39, wherein the strain amount and a strain amount which has been stored in advance are compared, and it is determined that the strain amount is abnormal in case the difference is sufficiently large.

57. The computer-readable recording medium having recorded therein a program that makes a computer execute a method of examining pattern defects according to claim 39, wherein the strain amount calculation step variably sets up the dimension for the estimation according to the contents of the compared images in estimating the strain amount.

* * * * *